(12) United States Patent
Tsuchiya et al.

(10) Patent No.: US 12,042,547 B2
(45) Date of Patent: Jul. 23, 2024

(54) METHOD FOR PRODUCING LUMINESCENT PARTICLES, LUMINESCENT PARTICLES, AND BIOIMAGING MATERIAL

(71) Applicant: KYULUX, INC., Fukuoka (JP)

(72) Inventors: Youichi Tsuchiya, Fukuoka (JP); Chihaya Adachi, Fukuoka (JP); Koudai Ikesue, Fukuoka (JP)

(73) Assignee: KYULUX, INC., Fukuoka (JP)

( * ) Notice: Subject to any disclaimer, the term of this patent is extended or adjusted under 35 U.S.C. 154(b) by 339 days.

(21) Appl. No.: 16/971,545

(22) PCT Filed: Feb. 20, 2019

(86) PCT No.: PCT/JP2019/006243
§ 371 (c)(1),
(2) Date: Aug. 20, 2020

(87) PCT Pub. No.: WO2019/163808
PCT Pub. Date: Aug. 29, 2019

(65) Prior Publication Data
US 2020/0397921 A1    Dec. 24, 2020

(30) Foreign Application Priority Data

Feb. 20, 2018  (JP) ................. 2018-028152
May 23, 2018   (JP) ................. 2018-098573

(51) Int. Cl.
*A61K 49/00*     (2006.01)
*C09K 11/06*     (2006.01)
*B82Y 5/00*      (2011.01)

(52) U.S. Cl.
CPC ...... *A61K 49/0067* (2013.01); *A61K 49/0017* (2013.01); *C09K 11/06* (2013.01); *B82Y 5/00* (2013.01)

(58) Field of Classification Search
CPC ............ A61K 49/0067; A61K 49/0017; C09K 11/06; G01N 21/64; G01N 33/58; B82Y 40/00; B82Y 5/00; B82Y 15/00; B82Y 20/00
See application file for complete search history.

(56) References Cited

U.S. PATENT DOCUMENTS

2016/0101386 A1*   4/2016  Kumar ................ B01D 53/228
                                                           422/86

FOREIGN PATENT DOCUMENTS

| CN | 1493646 | A | 5/2004 | | |
|---|---|---|---|---|---|
| CN | 103702559 | A | 4/2014 | | |
| CN | 105400507 | A | 3/2016 | | |
| JP | 2006-199798 | A | 8/2006 | | |
| JP | 2009-190976 | A | 8/2009 | | |
| JP | 2010-529460 | A | 8/2010 | | |
| JP | 2011-029460 | A | 2/2011 | | |
| JP | 2011-052228 | A | 3/2011 | | |
| JP | 2016-199751 | A | 12/2016 | | |
| JP | 6323970 | B1 | 5/2018 | | |
| KR | 10-2008-0077877 | A | 8/2008 | | |
| KR | 10-2009-0026642 | A | 3/2009 | | |
| KR | 100913610 | B1 | * | 8/2009 | ............... B82B 3/00 |
| WO | 2008/154332 | A1 | 12/2008 | | |
| WO | 2014/136776 | A1 | 9/2014 | | |
| WO | 2016/111196 | A1 | 7/2016 | | |

OTHER PUBLICATIONS

Kim et al., Int. J. Pharm., 2004, 271, 1-2, p. 207-214. (Year: 2004).*
Augusto et al., J. Mater. Chem., 2010, 20, p. 1192-1197. (Year: 2010).*
Wang, Nature, 2014, 4, 4279. (Year: 2014).*
Adhikari et al., Langmuir, 2009, 25, p. 2402-2406. (Year: 2009).*
Tesfai et al. (Nano Lett., 2008, 8, p. 897-901). (Year: 2008).*
Mehes et al., Angew. Chem. Int. Ed., 2012, 51, p. 11311-11315. (Year: 2012).*
Mousseau et al., Nanoscale, 2017, 9, p. 14967-14978. (Year: 2017).*
Suryawanshi et al., Spectrochimica Acta Part A: Molecular and Biomolecular Spectroscopy, 2017, 183, p. 232-238. (Year: 2017).*
KR100913610B1, English translation, 2009. (Year: 2009).*
Nakanotani et al., Sci. Rep., 2013, 3, p. 2127. (Year: 2013).*
International Preliminary Report on Patentability of Chapter I for PCT International Application No. PCT/JP2019/006243, mailed Sep. 4, 2019, with English translation.
International Search Report and Search Opinion for PCT International Application No. PCT/JP2019/006243, mailed Sep. 4, 2019.
Hansch et al., A Survey of Hammett Substituent Constants and Resonance and Field Parameters, Chem. Rev., 91:165-195 (1991).
Qian et al., AIE Luminogens for Bioimaging and Theranostics: From Organelles to Animals, Chem, 3(1), 56-91 (2017).
Office Action dated Jan. 5, 2023 issued in the corresponding Chinese patent application No. 201980014148.1 with its English Machine Translation.
Office Action dated Feb. 14, 2023 issued in the corresponding Japanese patent application No. 2020-500983 with its English Machine Translation.
Chinese office action dated Jun. 30, 2023, corresponding to Chinese patent application No. 201980014148.1.
Office Action dated Mar. 12, 2024 issued in the corresponding Korean patent application No. 10-2020-7027037 with its English Machine Translation.

(Continued)

*Primary Examiner* — Michael G. Hartley
*Assistant Examiner* — Leah H Schlientz
(74) *Attorney, Agent, or Firm* — BROWDY AND NEIMARK, PLLC

(57) ABSTRACT

Luminescent particles with a maximum diameter of less than 100 μm are produced by stirring an emulsion material, including a host material, an organic luminescent material containing no heavy metal element, a surfactant and water, under conditions that melt the host material, thereby forming an emulsion, and then cooling the emulsion. This method can provide luminescent particles which are highly safe and which exhibit high luminous efficiency in water.

7 Claims, 3 Drawing Sheets

(56) References Cited

OTHER PUBLICATIONS

Reisch et al., "Fluorescent Polymer Nanoparticles Based on Dyes-:Seeking Brighter Tools for Bioimaging", Small, 12, No. 15, 1968-1992, 2016.
Li et al., "Thermally Activated Delayed Fluorescence Organic Dots (TADF Odots) for Time-Resolved and Confocal Fluorescence Imaging in Living Cells and In Vivo", Adv. Sci., 4, 1600166, 2017.

* cited by examiner

HEK293 CELLS AFTER ADDITION of EXAMPLE PARTICLES 1 and 24-HOUR INCUBATION (a)  (b)  (c)

HEK293 CELLS AFTER ADDITION of EXAMPLE PARTICLES 1 and 7-DAY (4-PASSAGE) CULTURE (d)  (e)  (f)

METHOD FOR PRODUCING LUMINESCENT PARTICLES, LUMINESCENT PARTICLES, AND BIOIMAGING MATERIAL

TECHNICAL FIELD

The present invention relates to a method for producing organic luminescent particles having high luminous efficiency, to the luminescent particles, and to a bioimaging material that uses the luminescent particles.

BACKGROUND ART

Luminescent particles can be dispersed in blood and conveyed to various body tissues, and can also be introduced into cells in vivo or in vitro, and therefore are expected to be applied in the biochemical field, such as bioimaging materials. With a view to establishing such application, various types of luminescent particles have been researched and developed.

For example, the use of fine particles, comprising quantum dots or a lanthanoid complex, as a bioimaging material has been proposed (see, for example, patent literatures 1 and 2). Quantum dots are luminescent nanoparticles composed of inorganic semiconductor crystals such as CdSe, InP or $CuInS_2$, and are known to have high luminous efficiency and high light stability. However, such quantum dots are susceptible to degradation by active oxygen species in cells, and are therefore not suited for long-term cell tracing. In addition, such quantum dots entail problems such as a harmful effect of a heavy metal ion on a living body, their cytotoxicity, etc. The lanthanoid complex comprises a lanthanoid metal ion, such as $Sm^{3+}$ or $Eu^{2+}$, and an organic ligand. Thus, there is a fear of a harmful effect of the heavy metal ion on a living body.

On the other hand, the use of water-soluble organic nanoparticles as a bioimaging material has been proposed (see, for example, patent literature 3 and non-patent literature 1). Water-soluble organic nanoparticles that are conventionally used are produced by a method which involves microparticulation of an organic dye, which exhibits association-induced luminescence, performed by application of ultrasonic waves to the organic dye in a liquid, and stabilization of the resulting fine particles with a surfactant. Unlike the quantum dots or the lanthanoid complex, the water-soluble organic nanoparticles do not contain any heavy metal element, and thus have the advantage of high safety.

CITATION LIST

Patent Literature

Patent literature 1: Japanese Patent Laid-Open Publication No. 2009-190976
Patent literature 2: Japanese Patent Laid-Open Publication No. 2006-199798
Patent literature 3: Chinese Patent Publication No. CN105400507A

Non-Patent Literature

Non-Patent literature 1: J. Qian and B. Z. Tang, Chem (2017), 3(1), 56-91

SUMMARY OF THE INVENTION

Problems to be Solved by the Invention

As described above, organic luminescent particles such as water-soluble organic nanoparticles, which do not contain any heavy metal element, are highly safe and have promise as a bioimaging material. However, the present inventors' evaluation of the luminescence properties of water-soluble organic nanoparticles produced by the conventional method has revealed that the luminous efficiency is not sufficiently high; in particular, the luminous efficiency tends to be significantly lower in water than in a non-polar solvent. This is considered to be due to the fact that in a polar solvent such as water, the charge-separated state of a dye is stabilized by solvation and the non-radiation deactivation is accelerated, whereby the fluorescence is quenched. To have a sufficiently high luminous efficiency in water is essential to a bioimaging material to be used for an aqueous object such as a living body or cells. The conventional water-soluble organic nanoparticles do not appear fully satisfactory in this respect.

The present inventors have conducted intensive studies with a view to provide a method for producing luminescent particles which contain no heavy metal element, exhibit high luminous efficiency in water, and have high light stability, and to provide such luminescent particles. The present inventors have also conducted intensive studies with a view to provide a bioimaging material which uses the luminescent particles which are therefore highly safe and enable clear imaging of the distribution or the dynamics of living cells or a biological substance.

Means for Solving the Problems

The present inventors, through the intensive studies conducted to achieve the above objects, have now found that organic luminescent particles having high luminous efficiency and high light stability can be obtained by stirring an emulsion material including a host material, an organic luminescent material containing no heavy metal element, a surfactant, and water under conditions that melt the host material, thereby forming an emulsion, and then cooling the emulsion. The present invention has been made based on the finding, and has the following features:

[1] A method for producing luminescent particles with a maximum diameter of less than 100 comprising the steps of: stirring an emulsion material, including a host material, an organic luminescent material containing no heavy metal element, a surfactant and water, under conditions that melt the host material, thereby forming an emulsion; and then cooling the emulsion.

[2] The method for producing luminescent particles as described in [1], further comprising a step of drying a liquid mixture including the host material, the organic luminescent material containing no heavy metal element, and the surfactant, and then adding water to the dried mixture and stirring the resulting mixture, thereby obtaining the emulsion material.

[3] The method for producing luminescent particles as described in [2], wherein ultrasonic waves are applied to the resulting mixture being stirred.

[4] The method for producing luminescent particles as described in any one of [1] to [3], wherein the emulsion formed is an oil-in-water emulsion.

[5] The method for producing luminescent particles as described in any one of [1] to [4], wherein the cooling step includes a step of lowering the temperature of the emulsion at a rate of not less than 1° C./min.

[6] The method for producing luminescent particles as described in any one of [1] to [5], wherein the molten host material undergoes a glass transition in the cooling step.

[7] The method for producing luminescent particles as described in any one of [1] to [6], wherein the stirring of the emulsion material under conditions that melt the host material is performed while applying ultrasonic waves to the emulsion material.

[8] The method for producing luminescent particles as described in any one of [1] to [7], further comprising a step of sorting particles by size.

[9] The method for producing luminescent particles as described in any one of [1] to [8], further comprising a step of removing an excess of the surfactant after the step of cooling the emulsion.

[10] The method for producing luminescent particles as described in any one of [1] to [9], wherein the water is degassed water which has undergone inert gas replacement.

[11] The method for producing luminescent particles as described in any one of [1] to [10], wherein all the steps are performed under an inert gas atmosphere.

[12] The method for producing luminescent particles as described in any one of [1] to [11], wherein the emulsion material further includes an assist dopant.

[13] Luminescent particles produced by the production method as described in any one of [1] to [12].

[14] Luminescent particles with a maximum diameter of less than 100 μm, comprising a glassy host material, an organic luminescent material containing no heavy metal element, and a surfactant.

[15] The luminescent particles as described in [14], wherein the organic luminescent material is a delayed fluorescence material.

[16] The luminescent particles as described in [14] or [15], wherein the host material is a compound having a structure in which a benzene ring or a biphenyl ring is substituted by a carbazolyl group.

[17] The luminescent particles as described in any one of [14] to [16], further comprising an assist dopant.

[18] The luminescent particles as described in [17], wherein the assist dopant is a delayed fluorescence material.

[19] The luminescent particles as described in any one of [14] to [18], wherein the surfactant is a derivative of a glycerophospholipid.

[20] The luminescent particles as described in any one of [14] to [19], wherein the molar content ratio of the host material to the surfactant (host material/surfactant) is not less than 20.

[21] A bioimaging material comprising the luminescent particles as described in any one of [13] to [20].

Advantageous Effects of the Invention

The luminescent particle production method of the present invention can produce luminescent particles which, despite no inclusion of any heavy metal element, exhibit high luminous efficiency even in water and have high light stability. The bioimaging material of the present invention comprises the thus-produced luminescent particles, which are highly safe and enable clear imaging of the distribution or the dynamics of living cells or a biological substance.

DESCRIPTION OF THE EMBODIMENTS

Figure 1:
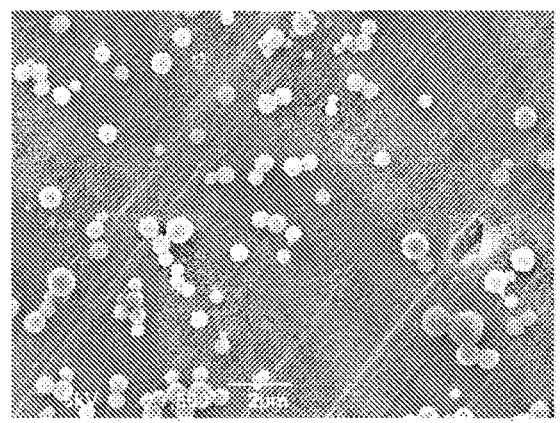
FIG. 1 is a scanning electron micrograph of example particles 1.

Embodiments of the present invention will now be described in detail. While the following description may be given of typical embodiments or specific examples of the present invention, the present invention is not intended to be limited to the embodiments or examples. As used herein, a numerical range as defined by an upper limit and a lower limit should be construed to include the upper limit and the lower limit. There is no particular limitation on the isotopic species of a hydrogen atom that exists in the molecule of a compound usable in the present invention. Thus, for example, all the hydrogen atoms in a molecule may be $^1H$, or part or all of the hydrogen atoms may be $^2H$ (deuterium D).

<Method for Producing Luminescent Particles>

The luminescent particle production method of the present invention is a method for producing luminescent particles with a maximum diameter of less than 100 μm, and comprises the steps of: stirring an emulsion material, including a host material, an organic luminescent material containing no heavy metal element, a surfactant and water, under conditions that melt the host material, thereby forming an emulsion; and then cooling the emulsion.

The luminescent particles produced by the production method of the present invention are luminescent particles having a maximum diameter of less than 100 μm. The "maximum diameter" of the luminescent particles in the present invention refers to the maximum diameter of the luminescent particles, measured by observation with a scanning electron microscope. In the case where the diameters of the luminescent particles cannot be measured by observation with a scanning electron microscope, the maximum mode diameter in a volume frequency distribution as measured by dynamic light scattering is taken as the "maximum diameter" of the luminescent particles in the present invention. In the production method of the present invention, the luminescent particles are produced in the form of agglomerated particles. Part or all of the agglomerated particles produced may have a maximum diameter of less than 100 μm; however, it is preferred that all of the agglomerated particles have a maximum diameter of less than 100 μm. The maximum diameter of the luminescent particles is preferably less than 10 μm, more preferably less than 1 μm, even more preferably less than 100 nm, still more preferably less than 50 nm, and particularly preferably less than 10 nm.

There is no particular limitation on the shape of the luminescent particles; the shape of the luminescent particles may be any of a spherical shape, a spheroidal shape, a rod-like shape, a geometric shape, an irregular shape, etc. A spherical shape or a spheroidal shape is preferred. In the case of a spherical luminescent particle, the diameter corresponds to the maximum diameter, while in the case of a luminescent particle having another shape, the length in the long axis direction corresponds to the maximum diameter.

In the luminescent particle production method of the present invention, when manufacturing such luminescent particles, an organic luminescent material containing no heavy metal element is used as a luminescent material, and therefore the resulting luminescent particles do not contain any heavy metal element. The use of the luminescent particles can avoid a harmful effect of a heavy metal element on a living body and the problem of cytotoxicity, which would occur with the use of quantum dots or a lanthanoid complex.

In the present invention, after an emulsion is formed by stirring an emulsion material including a host material, an organic luminescent material containing no heavy metal element, a surfactant, and water under conditions that melt the host material, the emulsion is cooled. It appears that during cooling and solidification of the molten host material, the luminescent molecules of the organic luminescent material become doped in the matrix of the host material to form a host/guest structure. Thus, in the resulting luminescent particles, the luminescent molecules are isolated from the influence of the external environment. Accordingly, the molecular structure and the special positions of the luminescent molecules are held stably even in a polar solvent such as water. In addition, association of the luminescent material can be prevented. This can achieve high luminous efficiency and high light stability, and can prevent the emission wavelength from becoming longer.

The respective steps of the luminescent particle production method of the present invention will now be described in detail.

[1] Emulsion Formation Step

In this step, an emulsion material including a host material, an organic luminescent material containing no heavy metal element, a surfactant, and water is stirred under conditions that melt the host material, thereby forming an emulsion. In particular, the organic luminescent material is dissolved in the molten host material, whereby an oily mixture is formed. Droplets of the oily mixture are dispersed in water. Thus, an oil-in-water (O/W) emulsion, consisting of the oily mixture of the host material and the organic luminescent material as liquid particles (dispersoid) and water as a dispersion medium, is formed. The surfactant functions as an emulsifier for stabilizing the emulsion.

The respective materials that constitute the emulsion material will now be described.

(Host Material)

The "host material" in the present invention refers to a material which is composed of an organic compound, which constitutes the liquid particles of the emulsion and also constitutes the luminescent particles obtained by the production method of the present invention, and whose content in the emulsion material is higher than the content of the organic luminescent material. The content (by weight) of the host material in the emulsion material is preferably at least 5 times, more preferably at least 10 times, even more preferably at least 20 times the content (by weight) of the organic luminescent material. The matrix of the host material in such an amount can securely isolate the luminescent particles from the influence of the external environment.

The host material for use in the present invention is preferably an organic compound of which at least one of the lowest excited singlet energy level and the lowest excited triplet energy level is higher than that of the organic luminescent material, more preferably an organic compound of which both of the lowest excited singlet energy level and the lowest excited triplet energy level are higher than those of the organic luminescent material. This makes it possible to effectively transfer the lowest excited singlet energy and the lowest excited triplet energy, generated in the host material, to the organic luminescent material, and to confine the lowest excited singlet energy and the lowest excited triplet energy, generated in the organic luminescent material, in the molecules of the organic luminescent material, thereby exploiting the full luminous efficiency.

Further, the host material is preferably an organic compound which can be a glassy state. This makes it possible to prevent scattering of light in the host material and efficiently draw radiant light from the organic luminescent material to the outside while isolating the organic luminescent material from the influence of the external environment with the host material.

Whether the host material is an organic compound which can be a glassy state can be determined by differential scanning calorimetry analysis. The glass transition temperature Tg of the host material is preferably 30 to 150° C., more preferably 40 to 100° C., and even more preferably 50 to 80° C. The glass transition temperature Tg refers to a temperature as measured with a differential scanning calorimeter.

From the viewpoint of performing the stirring of the emulsion material under conditions that melt the host material at a practical temperature, the melting point of the host material at atmospheric pressure is preferably 40 to 200° C., more preferably 50 to 100° C., and even more preferably 60 to 80° C. The melting point herein refers to a melting point as measured by differential thermal analysis. In the case where the melting point cannot be measured by differential thermal analysis, a value measured by differential scanning calorimetry analysis is taken as the melting point. In the case where the melting point cannot be measured by these methods, a value measured with a melting-point apparatus is taken as the melting point.

It is also preferred to use as the host material an organic compound having a melting point of less than the boiling point of water (i.e. less than 100° C.) at atmospheric pressure. Such a host material can be melted without boiling water at atmospheric pressure or even at reduced pressure. This makes it possible to use a simple heating device upon the stirring of the emulsion material under conditions that melt the host material, or to perform the stirring at a low temperature and a low pressure.

The meting point of an organic compound can be controlled by the introduction of a substituent such as an alkyl group. Therefore, an alkylated derivative, obtained by introducing an alkyl group into a known host material, can be preferably used as a host material. The alkyl group, which is to be introduced for the control of the melting point, may be either linear, branched or cyclic. There is no particular limitation on the number of carbon atoms in the alkyl group; however, the number is preferably not less than 4, more preferably 6 to 18, and even more preferably 8 to 12. There is no particular limitation on the number of the alkyl groups introduced; the number may be one, or two or more. In the case of introducing two or more alkyl groups, the alkyl groups may be the same or different from each other.

The following is an exemplary compound which is preferable as the host material. The present invention should not be construed as limited to the particular compound to be used as the host material.

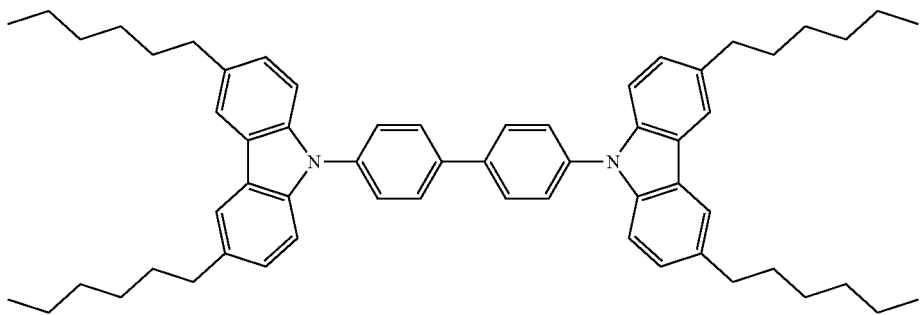 [SMILES: CCCCCCc1ccc2c(c1)c1cc(CCCCCC)ccc1n2-c1ccc(-c2ccc(-n3c4ccc(CCCCCC)cc4c4cc(CCCCCC)ccc43)cc2)cc1]

melting point: 96° C., Tg: 82° C.

The below-described exemplary compounds for use as host materials, other known host materials, and alkylated derivatives thereof can also be used. Among them, a compound having a structure in which an aromatic ring is substituted by a carbazolyl group is preferred, and a compound having a structure in which a benzene ring or a biphenyl ring is substituted by a carbazolyl group is more preferred.

(Organic Luminescent Material)

The "organic luminescent material containing no heavy metal element" in the present invention refers to a material which is composed of an organic compound that can radiate light when it deactivates from the excited state to the ground state, which, together with the host material, constitutes the liquid particles of the emulsion and also constitutes the luminescent particles obtained by the production method of the present invention, and which does not contain any heavy metal element. The "heavy metal element" herein refers to a metal element whose specific gravity as an elemental substance is not less than 4, and includes all of a heavy metal element constituting an elemental substance, a heavy metal element constituting an inorganic compound, a heavy metal element constituting a complex compound, and an ionized heavy metal element. The phrase "containing no heavy metal element" means substantially no content of a heavy metal element, and does not exclude unavoidable entry of a heavy metal element into the organic luminescent material. In particular, the phrase "containing no heavy metal element" means that the content of a heavy metal element is less than 10 ppm. The content of a heavy metal element is measured by ICP (Inductively Coupled Plasma) emission spectrometry. In the case where the content of a heavy metal element cannot be measured by ICP emission spectrometry, it can be measured by ICP mass spectrometry. The "organic luminescent material containing no heavy metal element" may be one which does not substantially contain any inorganic element. For example, an organic luminescent material composed solely of atoms selected from the group consisting of a carbon atom, a hydrogen atom, an oxygen atom, a nitrogen atom and a boron atom, an organic luminescent material composed solely of atoms selected from the group consisting of a carbon atom, a hydrogen atom, an oxygen atom and a nitrogen atom, an organic luminescent material composed solely of atoms selected from the group consisting of a carbon atom, a hydrogen atom and a nitrogen atom, or an organic luminescent material composed solely of atoms selected from the group consisting of a carbon atom, a hydrogen atom, a nitrogen atom and a boron atom, can be used as the "organic luminescent material containing no heavy metal element". The organic luminescent material is composed of an organic compound that can radiate light when it deactivates from the excited state to the ground state, and thus is distinguished from other materials such as a buffer solution and a surfactant.

There is no particular limitation on the type of the organic luminescent material for use in the present invention; any of a fluorescent material, a phosphorescent material other than a heavy metal complex, and a delayed fluorescence material, in particular a delayed fluorescence material can be used as the organic luminescent material.

The "delayed fluorescence material" refers to a material composed of an organic compound which can undergo reverse intersystem crossing from the excited triplet state to the excited singlet state, and radiates fluorescent light when it deactivates from the excited singlet state. The radiated fluorescent light is usually observed later than fluorescent light from the excited singlet state which has been reached through direct transition from the ground state, and therefore is called delayed fluorescence. When such a delayed fluorescence material is used as the organic luminescent material, not only the excited singlet energy but the excited triplet energy, through its conversion into the excited singlet energy, can also be effectively used for fluorescence emission, and therefore high luminous efficiency can be achieved. Furthermore, because of the luminescence effected through the reverse intersystem crossing, the time from the application of energy to the emission of light is long, and long-life luminescence can be achieved. The use of a thermally activated delayed fluorescence material (TADF material), which undergoes reverse intersystem crossing through the absorption of thermal energy, is especially preferred. A compound in which the difference $\Delta E_{ST}$ between the lowest excited singlet energy level ($E_{S1}$) and the lowest excited triplet energy level ($E_{T1}$) is not more than 0.3 eV or a compound in which the difference $\Delta E_{ST}$ is not more than 0.2 eV, for example, can be used as the delayed fluorescence material. It is preferred to use a compound in which the difference $\Delta E_{ST}$ is not more than 0.3 eV, preferably not more than 0.2 eV, and which has an aromatic ring substitute by at least one acceptor group (A) and at least one donor group (D) at particular positions. The acceptor group (A) refers to a substituent whose Hammett $\sigma_p$ value is positive, and the donor group (D) refers to a substituent whose Hammett $\sigma_p$ value is negative. For an explanation of the "Hammett $\sigma_p$ value", the Hammett values of the substituents, and specific examples of the substituent whose Hammett $\sigma_p$ value is positive and the substituent whose Hammett $\sigma_p$ value is negative, reference can be made to the description in Hansch, C. et al., Chem. Rev., 91, 165-195 (1991). The aromatic ring may be an aromatic hydrocarbon ring composed of carbon hydride, or an aromatic hetero ring containing a heteroatom, and may be a single ring or a condensed ring. A method for measuring the $\Delta E_{ST}$ and specific examples of the delayed fluorescence material will be described later.

In the luminescent particles obtained by the production method of the present invention, luminescence occurs from the organic luminescent material. The luminescence may be any of fluorescence emission, phosphorescence emission, and delayed fluorescence emission, and may be luminescence from an exciplex formed by association between a molecule of the organic luminescent material and a molecule of the host material. Part of the luminescence may be from the host material.

(Surfactant)

The surfactant functions to reduce the interfacial tension between the liquid particles, formed of the host material and the organic luminescent material, and water as a dispersion medium in the emulsion and, in addition, to form a protective film at the interface so as to stabilize the liquid particles in water.

A compound which does not react chemically with the host material or the organic luminescent material and which is free from the problem of cytotoxicity and is safe for a living body can be used as the surfactant. A non-ionic surfactant, an anionic surfactant or a natural surfactant can be preferably used.

The non-ionic surfactant may be one having an HLB of 6 to 18. Examples of such a non-ionic surfactant include sorbitan fatty acid esters such as sorbitan monocaprylate, sorbitan monolaurate and sorbitan monopalmitate; and glycerin fatty acid esters such as glycerin monocaprylate, glycerin monomyristate and glycerin monostearate; and their derivatives.

Examples of the anionic surfactant include alkyl sulfates having an alkyl group with 10 to 18 carbon atoms, such as sodium acetyl sulfate, sodium lauryl sulfate and sodium oleyl sulfate; polyoxyethylene alkyl ether sulfates in which the average number of moles of added ethylene oxide is 2 to 4 and the number of carbon atoms in the alkyl group is 10 to 18, such as sodium polyoxyethylene lauryl ether sulfate; alkyl sulfosuccinates in which the number of carbon atoms in the alkyl group is 8 to 18, such as sodium lauryl sulfosuccinate; and their derivatives.

Examples of the natural surfactant include lecithins and glycerophospholipids; sphingophospholipids such as sphingomyelin; sucrose fatty acid esters in which the fatty acid moiety has 12 to 18 carbon atoms; and their derivatives.

Among them, a glycerophospholipid derivative is preferred, a derivative of a compound in which ethanol amine is phosphoester-linked to a glycerophospholipid is more preferred, and a phospholipid modified with amine-terminated PEG (polyethylene glycol) having a structure in which polyethylene glycol is linked to the ethanol amine is even more preferred.

Such a phospholipid modified with amine-terminated PEG can be exemplified by a compound represented by the following general formula (A):

General formula (A)

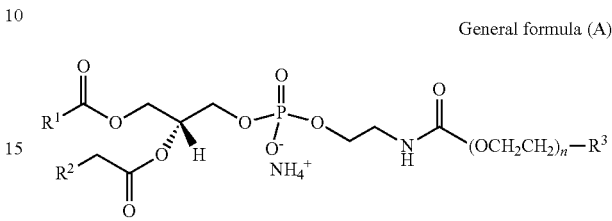

In the general formula (A), $R^1$ and $R^2$ each independently represent a substituted or unsubstituted alkyl group, and $R^3$ represents a substituent. n is an integer of 1 to 500.

The alkyl groups of $R^1$ and $R^2$ may be either linear or branched, preferably linear. The number of carbon atoms in each alkyl group is preferably 1 to 30, more preferably 6 to 25, and even more preferably 10 to 20. While the alkyl groups may be substituted by a substituent, they are preferably unsubstituted. $R^1$ and $R^2$ may be the same or different from each other; however, they are preferably the same.

The substituent of $R^3$ can be exemplified by a substituted or unsubstituted alkoxy group, and a substituted or unsubstituted amino group. Though the alkoxy group may be substituted by a substituent, it is preferably unsubstituted. There is no particular limitation on the number of carbon atoms in the alkoxy group; however, it is preferably 1 to 20, more preferably 1 to 10, and even more preferably 1 to 5. While the amino group is preferably unsubstituted, it is also preferable that the amino group be substituted by a substituent having a carbonyl group. In a specific example of a structure in which the amino group is substituted by a substituent having a carbonyl group, an amide linkage is formed through bonding between the nitrogen atom of the amino group and a carbonyl group, and a heterocyclic ring having a carbonyl group is linked to the amide linkage.

The following are exemplary compounds which are preferable as the surfactant. It should be noted that surfactants usable in the present invention are not limited to the exemplary compounds. In the following formulae, n is an integer of 1 to 500. The compounds for use as the surfactant may be used either singly or as a mixture thereof.

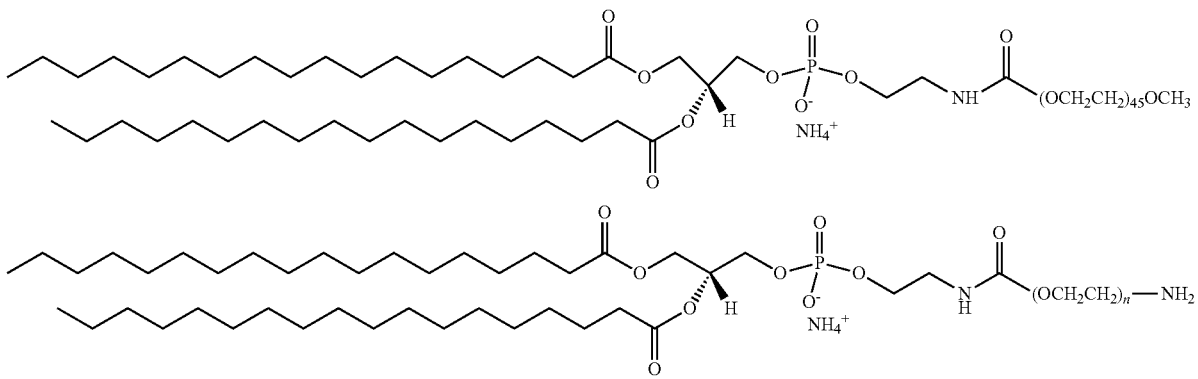

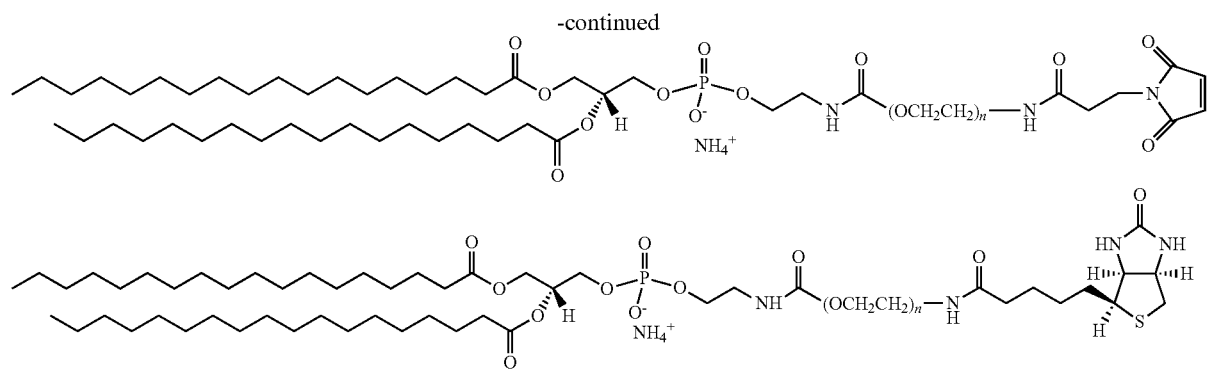

By controlling the concentraiton of the host material and the concentratrion of the surfactant in the emulsion material, the average and the variance (dispersion) of the particle size distribution of the resulting luminescent particles can be adjusted. In particular, the sizes (diameters) of the resulting luminescent particles depend on the concentraiton of the host material, the concentratrion of the surfactant, and the types of these materials. It is therefore preferred to appropriately select the type of the host material and the type of the surfactant, and appropriately adjust their concentrations depending on the types so that the intended particle size distribution will be obtained.

The sizes of the luminescent particles can be controlled to be small by setting the molar content ratio of the host material to the surfactant in the emulsion material at a low value. Luminescent particles having smaller sizes can be obtained by setting the molar content ratio of the host material to the surfactant at a low value, and adjusting the final concentrations of these materials in the aqueous dispersion to be low.

(Water)

Water serves as the dispersion medium of the emulsion.

Degassed water, water whose dissolved gas has been replaced with an inert gas such as argon, ultrapure water having a specific resistance of not less than 17 MΩ·cm, etc. are preferably used as the water of the emulsion. Among them, degassed water is more preferably used, and degassed water which has undergone inert gas replacement is even more preferably used. The use of degassed water can produce luminescent particles having high luminous efficiency and high light stability. Methods for producing degassed water may include a freezing/degassing method, a method for degassing water by boiling or depressurization, a method for degassing water by applying ultrasonic waves to the water, etc. Among them, the use of the freezing/degassing method is preferred.

The oxygen concentration in the degassed water is preferably not more than 5 ppm, more preferably not more than 1 ppm, and even more preferably not more than 0.1 ppm.

The amount of water is preferably 1 to 500000 times, more preferably 1000 to 10000 times, even more preferably 2500 to 5000 times the total amount of the host material, the organic luminescent material and the surfactant.

(Other Materials)

The liquid particles of the emulsion formed in the present invention and the luminescent particles obtained by the production method of the present invention may comprise a material(s) other than the host material, the organic luminescent material containing no heavy metal element, and the surfactant. Such other material can be exemplified by an assist dopant. The assist dopant is composed of an organic compound having a lowest excited singlet energy level intermediate between the lowest excited singlet energy level of the host material and the lowest excited singlet energy level of the organic luminescent material, and functions to assist the luminescence of the organic luminescent material. Thus, the luminescent particles using the assist dopant emit light mainly from the organic luminescent material; the luminescence from the assist dopant is preferably less than 10%, more preferably less than 1% of the overall luminescence from the luminescent particles. It is possible that no luminance from the assist dopant can be observed at all. A delayed fluorescence material is preferably used as the assist dopant. The delayed fluorescence material can convert the excited triplet energy into the excited singlet energy and supply the energy to the organic luminescent material. Thus, the delayed fluorescence material can effectively assist the fluorescence emission of the organic luminescent material. For an explanation, a preferable range and examples of the delayed fluorescence material, reference can be made to the above explanation, preferable range and examples of the delayed fluorescence material for use as the organic luminescent material. A compound composed solely of atoms selected from the group consisting of a carbon atom, a hydrogen atom, an oxygen atom and a nitrogen atom, or a compound composed solely of atoms selected from the group consisting of a carbon atom, a hydrogen atom and a nitrogen atom, for example, can be used as the assist dopant.

When the assist dopant is added to the emulsion, the amount of the assist dopant is preferably more than 5% by weight, more preferably more than 10% by weight, even more preferably more than 15% by weight based on the total amount of the host material and the organic luminescent material. Further, the amount of the assist dopant is preferably less than 50% by weight, more preferably less than 30% by weight, even more preferably less than 20% by weight based on the total amount of the host material and the organic luminescent material.

A second host material, which can form an exciplex with the above host material and emit light, may be used as another material. The use of the second host material can enhance the luminous efficiency and light stability of the resulting luminescent particles. An organic compound which has a different structure from the above host material and which has the fucntion as a host material, i.e. the function to isolate the luminescent molecules from the influence of the external environment can be used as the second host material. For preferable ranges and examples of organic compounds usable as the second host material, reference can be made to the description under the heading "Host Material".

(Emulsion Formation Conditions)

In the present invention, an emulsion is formed by stirring an emulsion material, including the host material, the organic luminescent material containing no heavy metal element, the surfactant and water, under conditions that melt the host material. For each of the host material, the organic luminescent material containing no heavy metal element, and the surfactant, either a single material or a combination of two or more materials may be used.

There is no particular limitation on a procedure for preparing the emulsion material; however, it is preferred to prepare the emulsion material by first drying a liquid mixture including the host material, the organic luminescent material and the surfactant, and then adding water to the dried mixture and stirring the resulting mixture. This method can produce an emulsion in a good dispersion state. A mixed solvent is preferably used when preparing the liquid mixture including the host material, the organic luminescent material and the surfactant. For example, a mixed solvent of an alcohol and a polar solvent (having a solubility parameter of less than 10), as exemplified by a mixed solvent of methanol and chloroform, can be preferably used. The volumetric mixing ratio between the alcohol and the polar solvent is preferably 1:20 to 20:1, more preferably 1:9 to 9:1.

The particle diameter of the emulsion material can be controlled by applying ultrasonic waves to the emulsion material in a state dispersed e.g. in water. The frequency of the ultrasonic waves is preferably 1 kHz to 100 kHz, more preferably 5 kHz to 80 kHz, and even more preferably 10 kHz to 60 kHz. The time for applying ultrasonic waves is preferably 1 minute to 240 minutes, more preferably 30 minutes to 180 minutes, and even more preferably 60 minutes to 120 minutes. The diameters of the luminescent particles can be reduced by increasing the ultrasonic wave application time. When control to reduce the diameters of the luminescent particles is performed by other means, such as by increasing the concentration of the surfactant upon the preparation of the emulsion material, luminescent particles having small diameters can be obtained even when the ultrasonic wave application time is short (or even without performing ultrasonic wave application).

The stirring of the emulsion material under conditions that melt the host material is performed by heating and melting the emulsion material, and stirring the emulsion material in the molten state. Any of a microwave heating method, a heater heating method and an induction heating method can be used for the heating of the emulsion material. When the melting point of the host material is higher than the boiling point of water at atmospheric pressure, it is preferred to heat the emulsion material and melt the host material at a high pressure in order to avoid boiling of water. An autoclave or a microwave irradiation apparatus can be used as an apparatus for heating the emulsion material at a high pressure. When heating the emulsion material at a high pressure, care should be taken so that water will not become a subcritical state or even a supercritical state. In particular, the critical point of water is 374° C., 22.1 MPa. The temperature and pressure in an autoclave should be controlled so that the internal atmosphere of the autoclave will not come close to or even exceed the critical point.

When the melting point of the host material at the pressure upon the heating is represented by $mp_h$, the heating temperature of the emulsion material is preferably in the range of $mp_h+0$ to $mp_h+50°$ C., more preferably in the range of $mp_h+1$ to $mp_h+20°$ C., and even more preferably in the range of $mp_h+2$ to $mp_h+10°$ C.

The melting point $mp_h$ herein refers to a melting point as measured by differential thermal analysis. In the case where the melting point cannot be measured by differential thermal analysis, a value measured by differential scanning calorimetry analysis is taken as the melting point. In the case where the melting point cannot be measured by these methods, a value measured with a melting-point apparatus is taken as the melting point.

The heating of the emulsion material will be sufficient if it is performed to such an extent that all the particles in the system being heated are melted. If the heating is performed more, the diameters of the resulting luminescent particles tend to increase. For example, when the emulsion material is heated by microwave irradiation, it is sufficient if the microwave irradiation is performed for a period of time that allows all the particles in the system to melt. If the microwave irradiation is continued for an additional time, then the diameters of the resulting luminescent particles will increase.

The stirring of the emulsion material can be performed by using a shaking apparatus, an ultrasonic wave application apparatus, a pressure type disperser, a propeller stirrer, a magnetic stirrer, or the like. The use of a shaking apparatus is preferred because a high recovery rate can be achieved. There is no particular limitation on the shaking conditions; the shaking conditions may be appropriately selected depending on the nature of the emulsion material. For example, it is preferred to use a stirring speed of 10 to 3000 rpm. The stirring of the emulsion material is preferably performed while applying ultrasonic waves to the emulsion material. This enables more efficient formation of the emulsion.

[2] Particle Diameter Control Step

In this step, the particle diameter of the emulsion formed in step [1] is controlled as necessary, whereby the diameters of the final luminescent particles can be controlled. The particle diameter control step may or may not be performed; however, it is preferred to perform the particle diameter control step. In particular, the particle diameter of the emulsion can be reduced by passing the liquid particles before solidification of the host material through a filter having a small pore size using a liposome production apparatus or an extruder, or by applying ultrasonic waves to the liquid particles as described above. The filter preferably has a pore size of not more than 200 nm, more preferably not more than 100 nm, and even more preferably not more than 50 nm.

This step corresponds to a pre-cooling particle sorting step in the below-described particle sorting step [4]. For the other conditions of this step, reference can be made to the description under the heading "[4] Particle Sorting Step".

[3] Cooling Step

In this step, the emulsion formed through the step [1], or the emulsion formed through the step [1] and the optional step [2] is cooled. The molten host material is solidified and the liquid particles are converted into solid particles, whereby solid luminescent particles including the host material and the organic luminescent material are obtained. The solidification of the host material by cooling preferably is glass transition from the liquid state to a glassy state. This can produce luminescent particles which are isolated by the host material from the influence of the external environment and which have high luminous efficiency.

The cooling may be performed by leaving the emulsion to stand after releasing the conditions that melt the host material, or by cooling the emulsion under controlled temperature-lowering conditions using a cooling apparatus. It is preferred to perform the cooling by using a cooling apparatus because high-quality luminescent particles can be produced efficiently.

The cooling step preferably includes a temperature-lowering step of lowering the temperature of the emulsion at a rate of not less than 1° C./min. This allows the molten host material to undergo a glass transition, thereby obtaining the host material in a glassy state. The temperature-lowering rate in the temperature-lowering step may be either constant during the entire step or changed over time. When the temperature-lowering step is employed, the entire emulsion cooling step may be performed by the temperature-lowering step, i.e. by lowering the temperature of the emulsion at a rate of not less than 1° C./min. Alternatively, the temperature-lowering step may be performed as part of the emulsion cooling step. The temperature-lowering rate in the temperature-lowering step is preferably 1 to 50° C./min, more preferably 1 to 20° C./min, and even more preferably 1 to 10° C./min.

The luminescent particles obtained by the above steps are dispersed in water as a dispersion medium. The surfactant is present in the water and on the surfaces of the luminescent particles. The surfactant contributes to stabilization of the luminescent particles. However, if the surfactant is present in excess, an excess of the surfactant is preferably removed from the aqueous dispersion of the luminescent particles. A method such as centrifugal separation, ultrafiltration, dialysis, or gel column chromatography can be used for the removal of the surfactant.

For the purpose of long-term storage or for making a sample adjustment depending on the intended use, the luminescent particles obtained by the above steps, which are dispersed in water as a dispersion medium, can be subjected to freeze-drying to obtain dried powder. Since the luminescent particles after freeze-drying have been stabilized by the surfactant, they have the same water dispersibility as before the freeze-drying and can be re-dispersed in any aqueous medium such as a buffer solution.

[4] Particle Sorting Step

In this step, the luminescent particles are sorted by size. The particle sorting step is an optional step to be performed as necessary, and may be a step of sorting out the luminescent particles having a predetermined range of diameter or a step of sorting the luminescent particles into different diameter ranges.

The particle sorting step may be performed after completion of the cooling step or, as with the above-described particle diameter control step [2], may be performed before the cooling step, or may be performed during the cooling step. The particle sorting step may be performed before or during the cooling step, and after the cooling step.

For example, the emulsion is passed through a coarse filter before or during the cooling step to remove large-diameter particles, and the filtrate that has passed through the filter is cooled, whereby particles having a more uniform diameter can be obtained. The sorting of particles before or during the cooling step can be performed by using a filter provided e.g. in a liposome production apparatus or an extruder, while the sorting of particles after the cooling step can be performed by using a method such as centrifugal separation or ultrafiltration.

The diameters of the luminescent particles to be sorted out in the particle sorting step may differ depending on the intended use. In the case where the luminescent particles are to be used as an imaging material, the average particle diameter of the sorted particles is preferably 10 to 500 nm, more preferably 10 to 350 nm, even more preferably 10 to 200 nm, sill more preferably 10 to 100 nm, and particularly preferably 10 to 30 nm.

The "average diameter" of the luminescent particles herein refers to a hydrodynamic diameter as determined by cumulant analysis using a dynamic light scattering method. An average particle diameter as determined by volume frequency distribution analysis may also be used. In the case where the average particle diameter cannot be measured by a dynamic light scattering method, an average particle diameter as determined by volume frequency distribution analysis of a scanning electron micrograph using an imaging method is taken as the "average diameter" of the luminescent particles.

[Luminescent Particle Production Atmosphere]

The above-described luminescent particle production steps are preferably performed in a low-oxygen atmosphere in which the oxygen concentration is lower than air. In particular, the steps before the cooling step are preferably performed in a low-oxygen atmosphere because in those steps the organic luminescent material has not yet been protected by the matrix of the host material. This can produce luminescent particles having high luminous efficiency and high light stability. Luminescent particles having higher light stability can be obtained by performing the production process under thorough low-oxygen conditions, for example by preparing the emulsion using the above-described degassed water, and performing at least all the steps before the cooling step in a low-oxygen atmosphere. The low-oxygen atmosphere can be exemplified by a space in which air is replaced with an inert gas such as argon or nitrogen, or a stream of such an inert gas.

The oxygen concentration of the low-oxygen atmosphere for use in the production of luminescent particles is preferably not more than 5 ppm, more preferably not more than 1 ppm, and even more preferably not more than 0.1 ppm.

<Luminescent Particles>

The luminescent particles of the present invention will now be described.

The luminescent particles of the present invention are characterized in that they are produced by the luminescent particle production method of the present invention.

For an explanation of the luminescent particle production method of the present invention, reference can be made to the description under the heading "Method for Producing Luminescent Particles".

The luminescent particles of the present invention are luminescent particles with a maximum diameter of less than 100 μm, comprising a glassy host material, an organic luminescent material containing no heavy metal element, and a surfactant.

For an explanation, preferable ranges and examples of the host material, the organic luminescent material containing no heavy metal element, the surfactant, optional other materials to be added as necessary, and the maximum diameter of the luminescent particles, reference can be made to the relevant description under the heading "Method for Producing Luminescent Particles".

The "glassy host material" in the present invention refers to a host material which is at least partly in a glassy state. The host material, constituting the luminescent particles, may be in the glassy state either entirely or partly. The host material, constituting the luminescent particles, preferably does not contain any crystals or microcrystals. Whether the host material is in a glassy state can be determined by differential scanning calorimetry analysis. The use of such a glassy host material makes it possible to prevent scattering of light in the host material and efficiently draw radiant light from the organic luminescent material to the outside while isolating the organic luminescent material from the influence of the external environment with the host material. Therefore, the luminescent particles of the present invention have high luminous efficiency and high light stability.

Further, the organic luminescent material containing no heavy metal element is used as a luminescent material in the luminescent particles of the present invention. This can avoid a harmful effect of a heavy metal element on a living body and the problem of cytotoxicity, which would occur in luminescent particles that use quantum dots, a lanthanoid complex, or a phosphorescent material containing a heavy metal complex.

In the luminescent particles of the present invention, the molar content ratio of the host material to the surfactant (host material/surfactant) is preferably not less than 20. Such luminescent particles have higher light stability.

The host material/surfactant molar content ratio can be measured by elemental analysis.

[Difference $\Delta E_{ST}$ Between the Lowest Excited Singlet Energy Level ($E_{S1}$) and the Lowest Excited Triplet Energy Level ($E_{T1}$)]

The difference $\Delta E_{ST}$ between the lowest excited singlet energy level ($E_{S1}$) and the lowest excited triplet energy level ($E_{T1}$) in a delayed fluorescence material for use in the luminescent particle production method of the present invention and in the luminescent particles of the present invention can be determined by calculating the lowest excited singlet energy level ($E_{S1}$) and the lowest excited triplet energy level ($E_{T1}$) by the following methods, and substituting the calculated values into the equation: $\Delta E_{ST}=E_{S1}-E_{T1}$.

(1) Lowest Excited Singlet Energy Level ($E_{S1}$)

A solution containing a measurement target compound and polymethyl methacrylate is prepared, and the solution is spin-coated onto an Si substrate to produce a 100 nm thick sample whose concentration of the measurement target compound is 0.5% by weight. The fluorescence spectrum of the sample is measured at room temperature (300 K), and the luminescence is integrated over a period of time from immediately after the incidence of excitation light to 100 nanoseconds after the incidence to obtain a fluorescence spectrum, with the ordinate axis representing emission intensity and the abscissa axis representing wavelength. A tangent line to a short wavelength-side rise of the emission spectrum is drawn, and a wavelength value $\lambda_{edge}$ [nm] at the intersection of the tangent line and the abscissa axis is determined. The wavelength value is converted by the following conversion formula into an energy value $E_{S1}$:

$E_{S1}[eV]=1239.85/\lambda_{edge}$   Conversion formula:

In the measurement of the emission spectrum, a nitrogen laser (MNL200, manufactured by Lasertechnik Berlin GmbH) can be used as an excitation light source, and a streak camera (C4334, manufactured by Hamamatsu Photonics K.K.) can be used as a detector.

(2) Lowest Excited Triplet Energy Level ($E_{T1}$)

The same sample as used for the determination of the lowest excited singlet energy level ($E_{S1}$) is cooled to 5 K, and the sample for phosphorescence measurement is irradiated with excitation light (337 nm), and the intensity of phosphorescence is measured using the streak camera. The luminescence is integrated over a period of time from 1 millisecond after the incidence of excitation light to 10 milliseconds after the incidence to obtain a phosphorescence spectrum, with the ordinate axis representing emission intensity and the abscissa axis representing wavelength. A tangent line to a short wavelength-side rise of the phosphorescence spectrum is drawn, and a wavelength value $\lambda_{edge}$ [nm] at the intersection of the tangent line and the abscissa axis is determined. The wavelength value is converted by the following conversion formula into an energy value $E_{T1}$:

$E_{T1}[eV]=1239.85/\lambda_{edge}$   Conversion formula:

The tangent line to the short wavelength-side rise of the phosphorescence spectrum is drawn in the following manner. In a wavelength range from the shortest wavelength to the wavelength of a peak in the phosphorescence spectrum, the peak being the shortest-wavelength one of all the peaks in the spectrum, the inclination of tangent line to the curve of the spectrum first increases and then decreases with increase in the wavelength of the tangent point. The tangent line at the point on the curve of the spectrum at which the tangent inclination is maximum is herein defined as the tangent line to the short wavelength-side rise of the phosphorescence spectrum.

The above shortest-wavelength peak does not include a peak whose intensity is less than 10% of the maximum peak intensity in the spectrum. Thus, the tangent line at the point on the curve of the spectrum at which the tangent inclination is maximum and which is closest to the shortest-wavelength peak is herein defined as the tangent line to the short wavelength-side rise of the phosphorescence spectrum.

[Exemplary Compounds of Delayed Fluorescence Material and Host Material]

The following is a description of specific examples of delayed fluorescence materials and host materials which can be preferably used in the luminescent particle production method of the present invention and in the luminescent particles of the present invention. It is to be noted, however, that materials usable in the present invention are not limited to the below-described exemplary compounds.

There is no particular limitation on the type and structure of the delayed fluorescence material that can be used as the organic luminescent material or as the assist dopant. For example, a delayed fluorescence material can be used which has a structure in which a donor group (typically a group having a negative Hammett $\sigma_p$ value) and an acceptor group (typically a group having a positive Hammett $\sigma_p$ value) are bonded to a linker (typically a conjugated linking group such as an aromatic group). In particular, a compound having a diarylamino group (the two aryl groups may be heteroaryl groups, or the two aryl groups may be linked to each other to form a structure such as a carbazolyl group) as a donor group, and a compound having, as an acceptor group, a group containing a cyano group or a heteroaryl ring can be preferably used. However, delayed fluorescence materials usable in the present invention are not limited to such compounds.

For example, delayed fluorescence materials having the following structures can be preferably used in the present invention. Among them, a compound having a structure in which dicyanobenzene is substituted by one or more 9-carbazolyl groups is preferred, and 4CzIPN, which is used in the Examples, is most preferred.

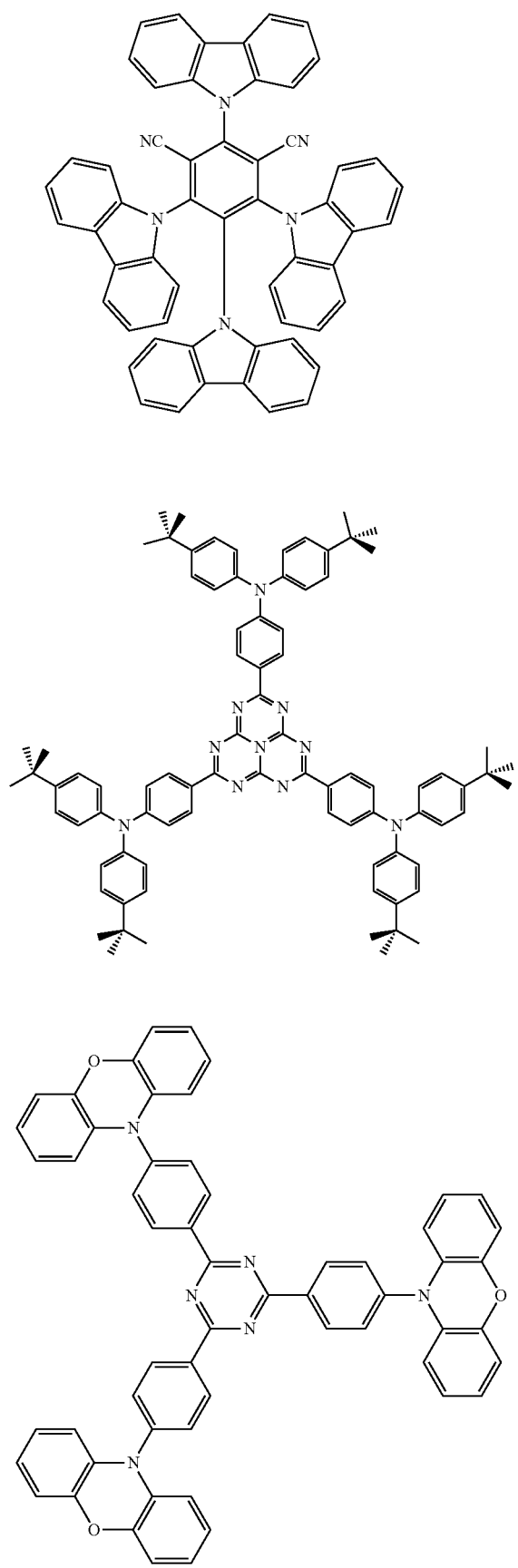
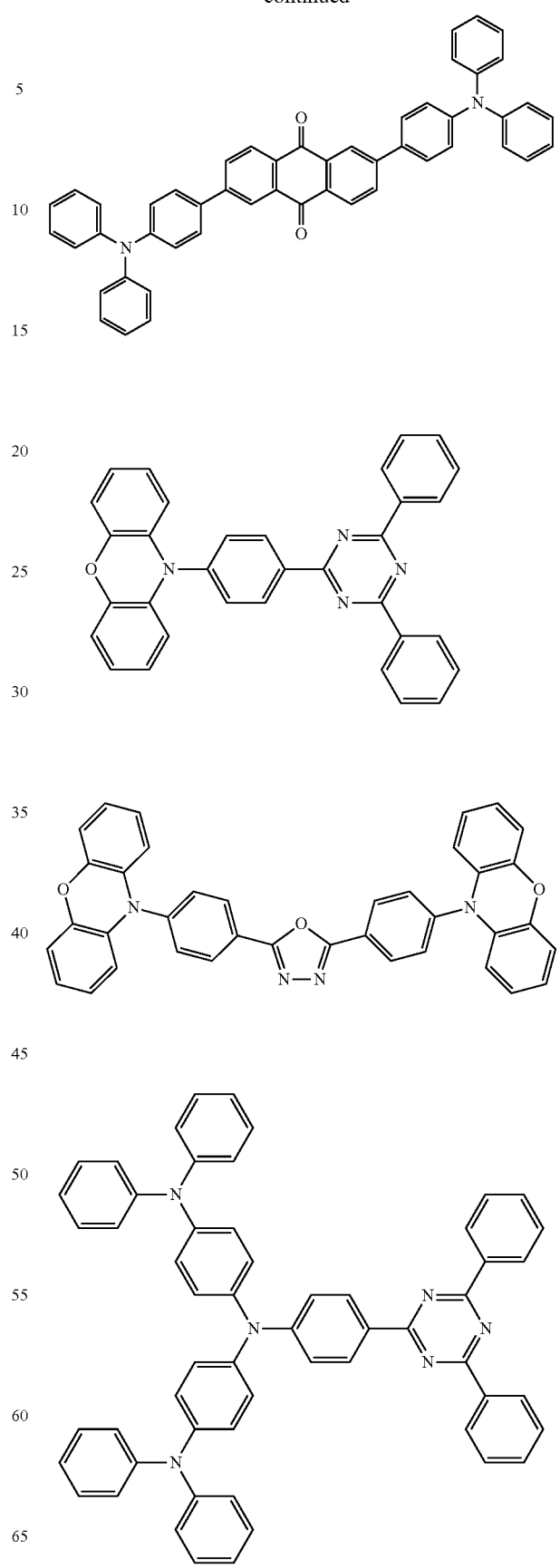

-continued

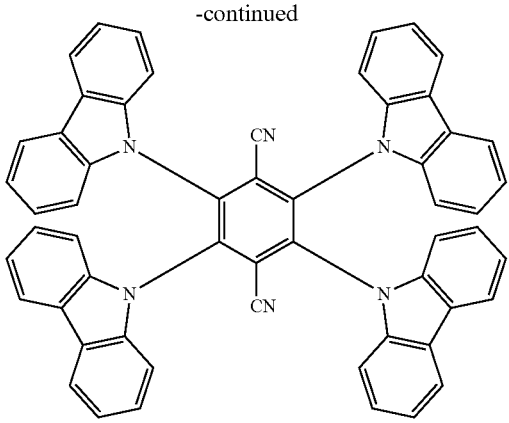

Examples of preferable delayed fluorescence materials include compounds of the general formulae, in particular enumerated compounds which radiate delayed fluorescence, described in paragraphs 0008 to 0048 and 0095 to 0133 of WO 2013/154064, paragraphs 0007 to 0047 and 0073 to 0085 of WO 2013/011954, paragraphs 0007 to 0033 and 0059 to 0066 of WO 2013/011955, paragraphs 0008 to 0071 and 0118 to 0133 of WO 2013/081088, paragraphs 0009 to 0046 and 0093 to 0134 of JP-A-2013-256490, paragraphs 0008 to 0020 and 0038 to 0040 of JP-A-2013-116975, paragraphs 0007 to 0032 and 0079 to 0084 of WO 2013/133359, paragraphs 0008 to 0054 and 0101 to 0121 of WO 2013/161437, paragraphs 0007 to 0041 and 0060 to 0069 of JP-A-2014-9352, and paragraphs 0008 to 0048 and 0067 to 0076 of JP-A-2014-9224. Examples of other preferable delayed fluorescence materials include luminescent materials which radiate delayed fluorescence, described in JP-A-2013-253121, WO 2013/133359, WO 2014/034535, WO 2014/115743, WO 2014/122895, WO 2014/126200, WO 2014/136758, WO 2014/133121, WO 2014/136860, WO 2014/196585, WO 2014/189122, WO 2014/168101, WO 2015/008580, WO 2014/203840, WO 2015/002213, WO 2015/016200, WO 2015/019725, WO 2015/072470, WO 2015/108049, WO 2015/080182, WO 2015/072537, WO 2015/080183, JP-A-2015/129240, WO 2015/129714, WO 2015/129715, WO 2015/133501, WO 2015/136880, WO 2015/137244, WO 2015/137202, WO 2015/137136, WO 2015/146541, and WO 2015/159541. The above patent documents enumerated in this paragraph are cited as part of the present description.

The following are exemplary compounds which can be preferably used as the host material of the luminescent particles. Alkylated derivatives of the exemplary compounds can also be preferably used as the host material.

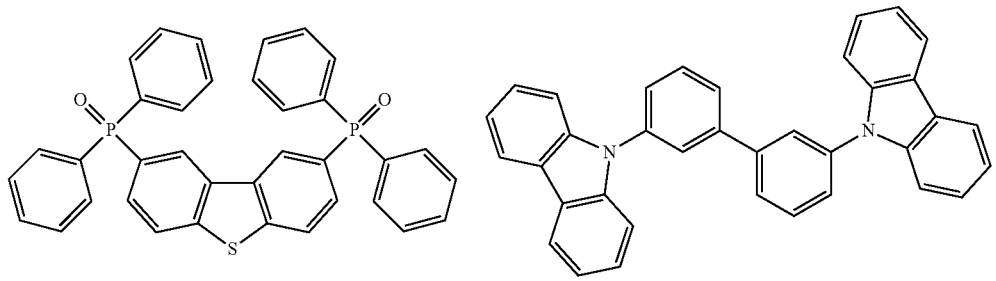

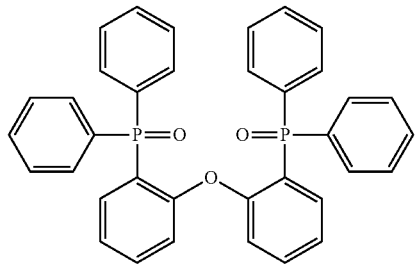

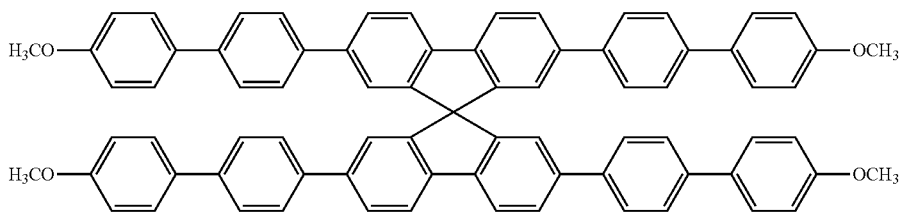

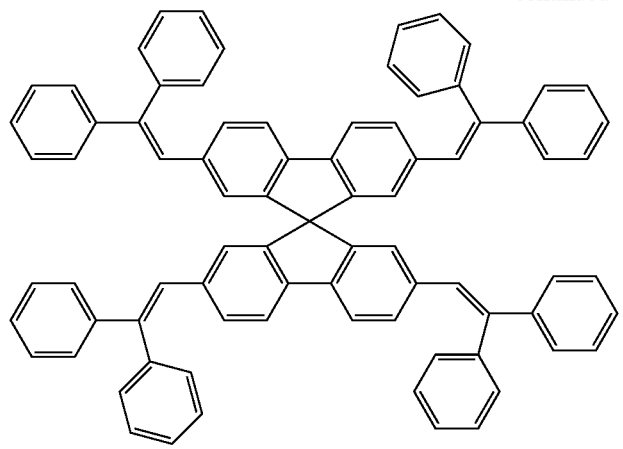
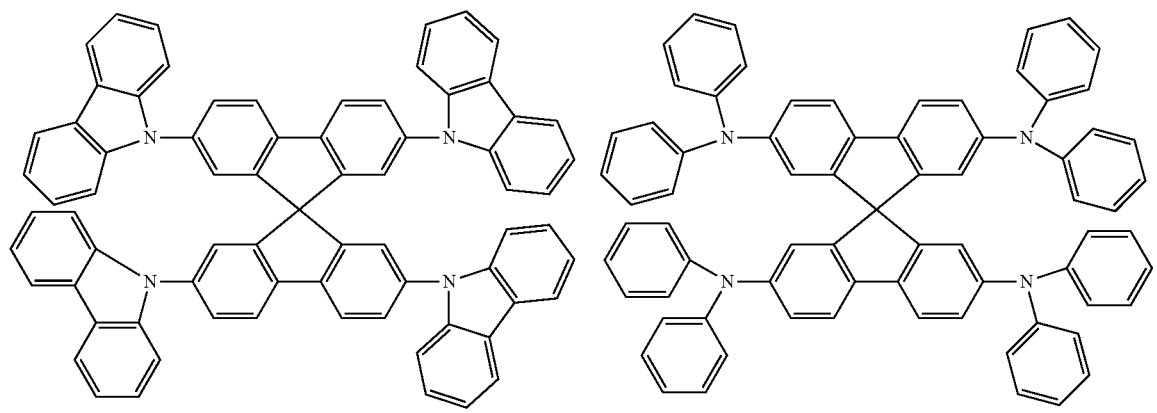
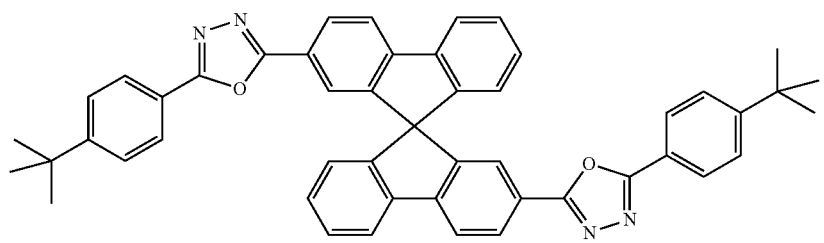
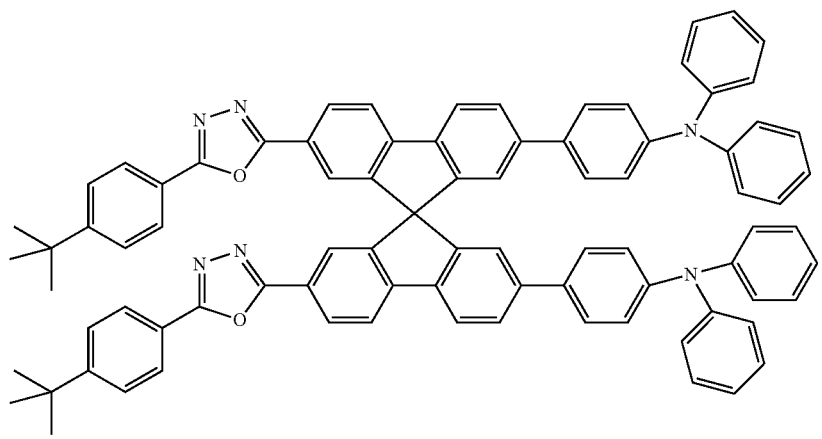

25 26
-continued
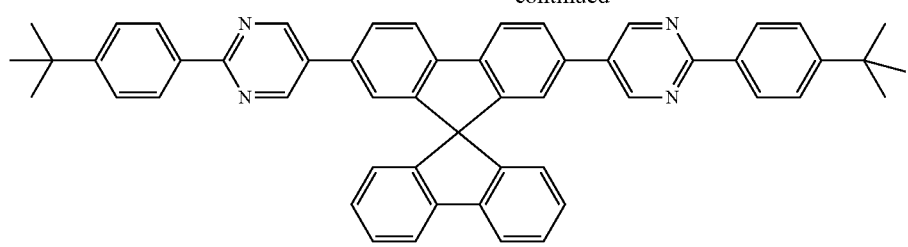
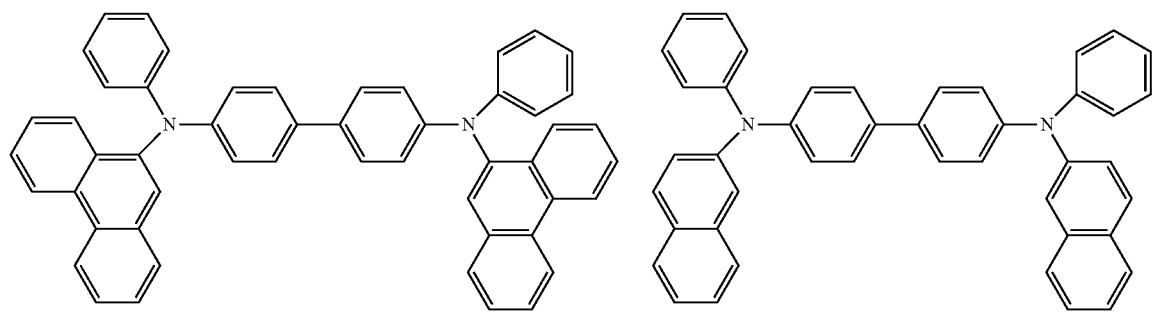
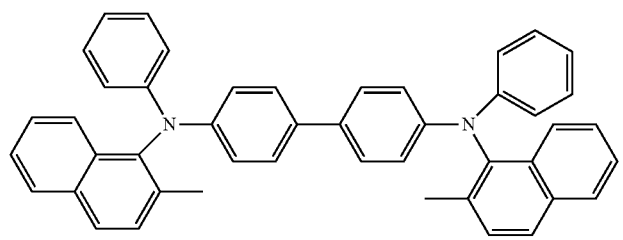
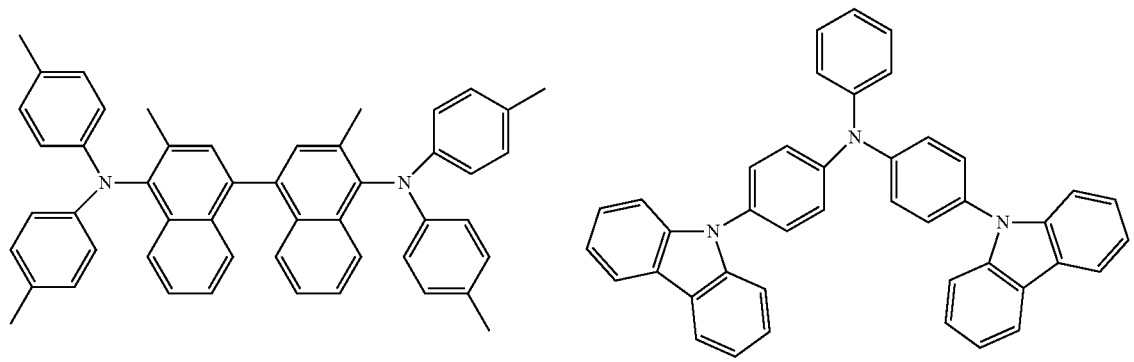

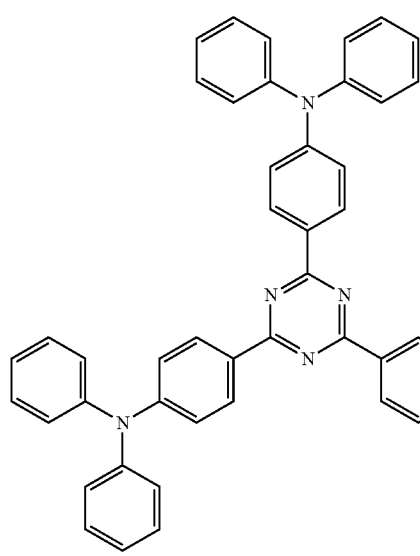
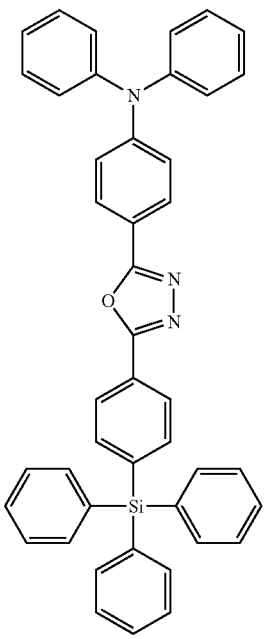
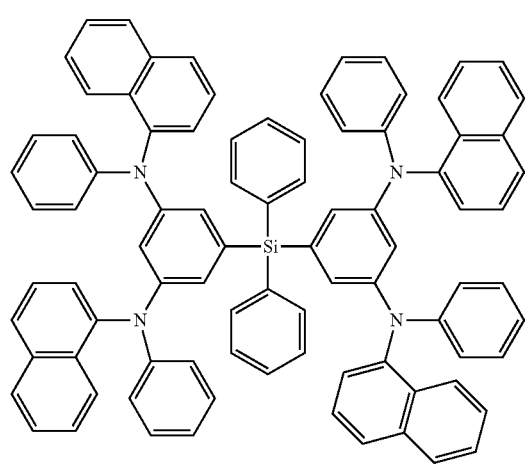
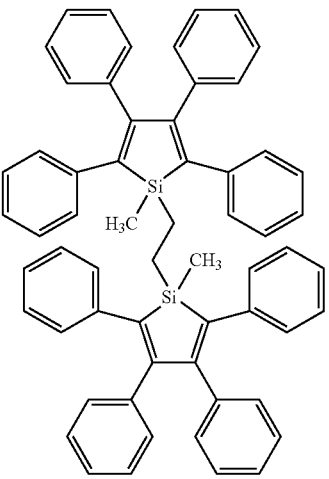
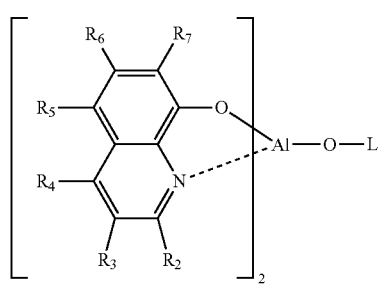
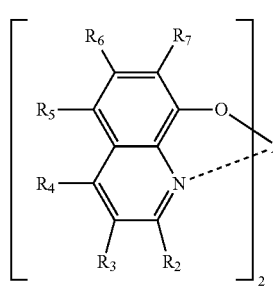
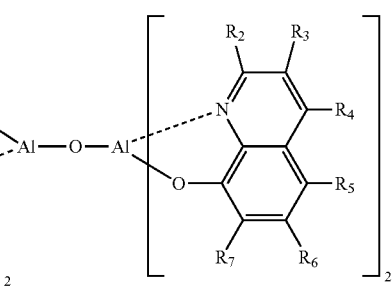
$R_2$-$R_7$ = H or substituent
L = ligand
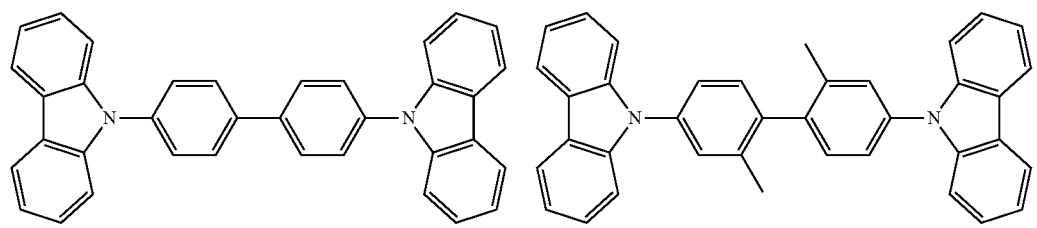

-continued
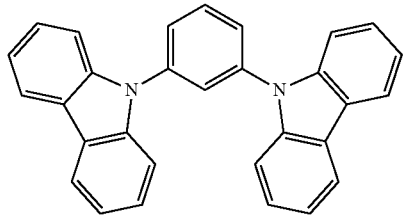 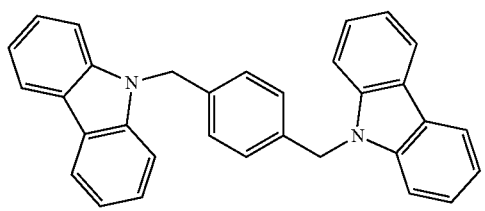
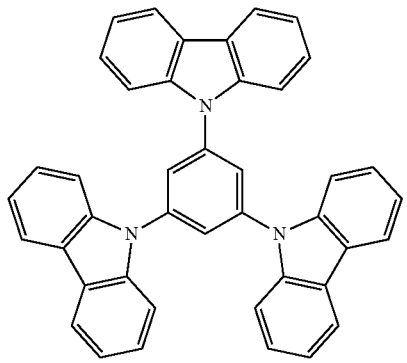 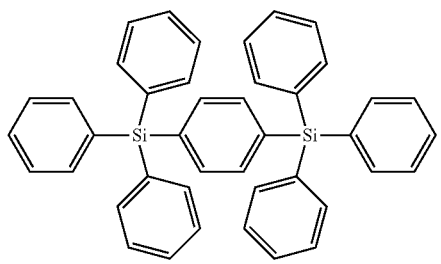
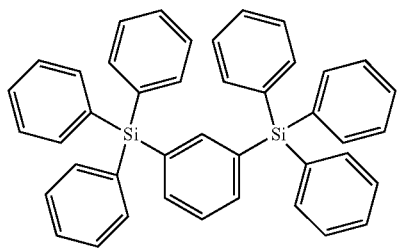 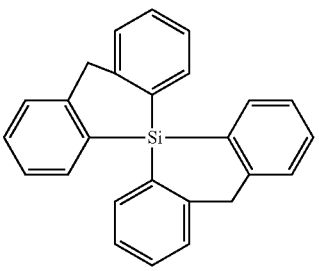
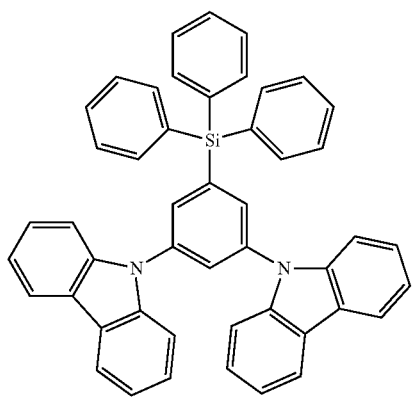 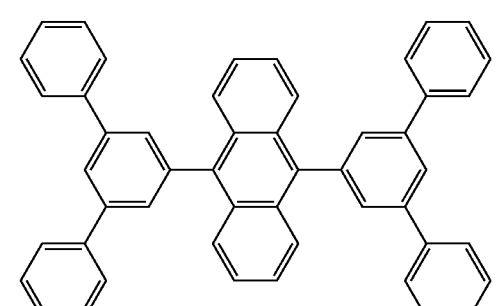
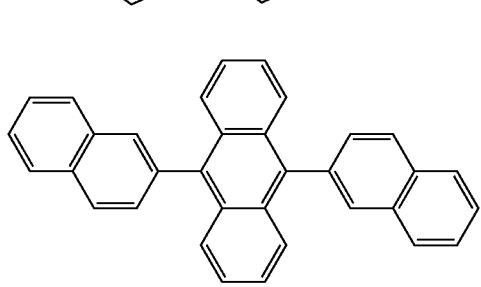 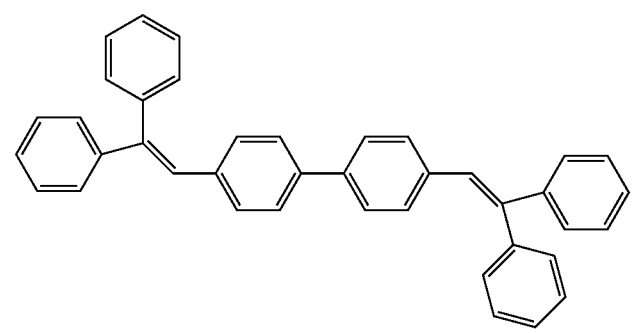

-continued
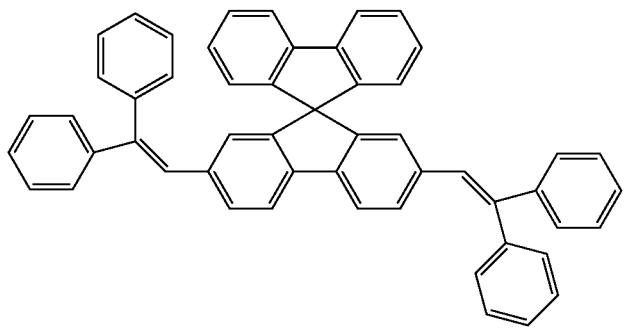
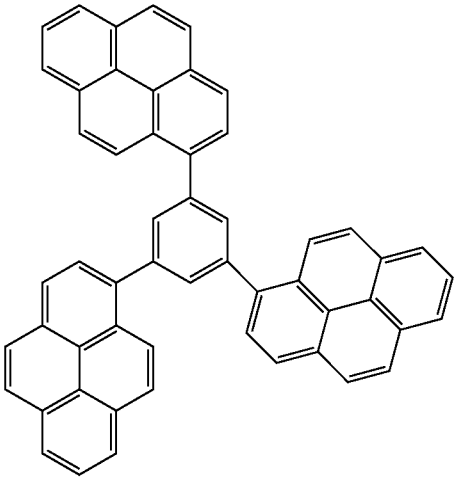
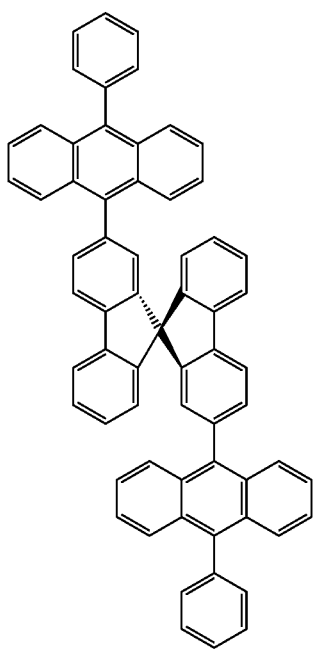
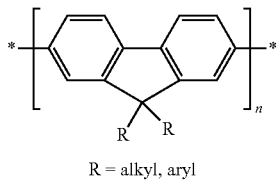
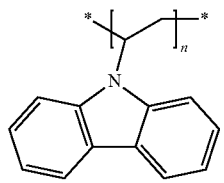
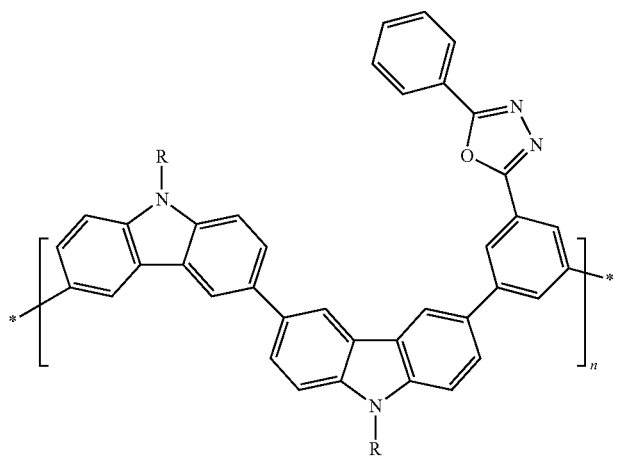
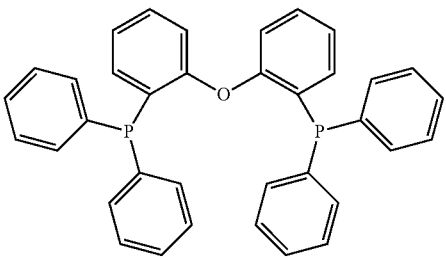

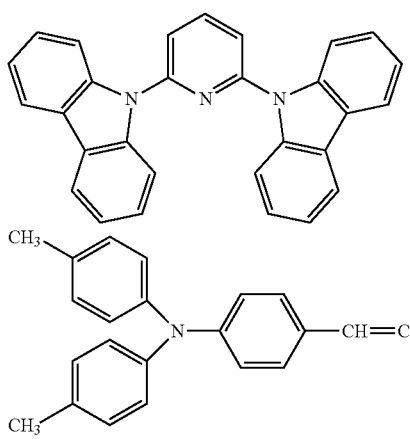

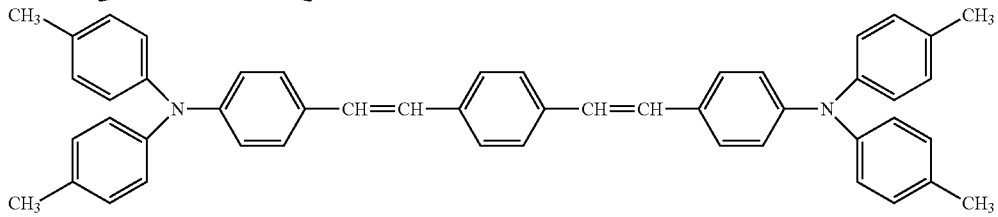

<Bioimaging Material>

The bioimaging material of the present invention will now be described.

The bioimaging material (composition) of the present invention comprises the luminescent particles of the present invention.

For an explanation of the luminescent particles of the present invention, reference can be made to the description under the heading "Luminescent Particles" as well as the description under the heading "Method for Producing Luminescent Particles".

As described above, the luminescent particles of the present invention are free from a harmful effect of a heavy metal element on a living body and the problem of cytotoxicity, and have high luminous efficiency and high light stability. Therefore, the bioimaging material of the present invention can be used safely both in vitro and in vivo, and enables clear imaging of the distribution or the dynamics of living cells or a biological substance.

For example, when the bioimaging material of the present invention is introduced into living cells such as cancer cells, nerve cells or stem cells, and then irradiated with excitation light, the luminescent particles introduced in the cells emit light. Imaging and analysis of the distribution or the dynamics of the cells can be performed by using the luminescence as an index. When the bioimaging material of the present invention is bound to a biological substance such as an enzyme, an antibody, a protein such as lectin, or DNA, and the labeled biological substance is either introduced into a living body or living cells or allowed to act on living cells, and then irradiated with excitation light, the luminescent particles bound to the biological substance emit light. Imaging and analysis of the distribution, the localization or the dynamics of the biological substance can be performed by using the luminescence as an index. The bioimaging material of the present invention can also be used as a labeling marker for an avidin-biotin system, and can therefore be used in the field of application of the avidin-biotin system, such as immunohistochemical staining, tissue multi-staining, etc.

EXAMPLES

The following examples illustrate the present invention in greater detail. It is to be understood that changes may be made to the below-described materials, processing manner, processing procedure, etc. without departing from the scope of the present invention. Thus, the present invention should not be construed as limited to the following examples. An evaluation of luminescence properties was performed by using an optical spectroscope (PMA-12, manufactured by Hamamatsu Photonics K.K.), and an observation of the shape of particles was performed by using a scanning electron microscope (Inspect S, manufactured by FEI). The average diameter and the polydispersion index of luminescent particles were determined by cumulant analysis using a dynamic light scattering measurement device (DLS-8000DL, manufactured by Otsuka Electronics Co., Ltd.).

(Example 1) Production of Luminescent Particles Using mCP (Host Material), 4CzIPN (Organic Luminescent Material), and DSPE-PEG2K (Surfactant)

mCP as a host material (melting point: 178° C.), 4CzIPN as an organic luminescent material, and DSPE-PEG2K (distearoylphophatidyl ethanolamine-polyethylene glycol 2000) as a surfactant were placed in a vial to prepare a liquid mixture. The contents of the respective materials, in terms of the final concentrations in an emulsion to be prepared, were as follows: mCP, 0.52 mM; 4CzIPN, 0.019 mM (6% by weight based on the total amount of mCP and 4CzIPN); and DSPE-PEG2K, 0.053 mM. The liquid mixture was dried such that a film was formed on the wall of the vial, and further dried overnight. 20 mL of water was added to the mixture and, while shaking the mixture, the mixture was incubated for 10 minutes, thereby peeling the film from the wall of the vial, and preparing an aqueous dispersion. While heating the emulsion material at 180° C. and at a high pressure below 20 bar by irradiating it with microwaves, it was stirred at 600 rpm for 10 minutes to form an emulsion, followed by cooling to obtain a suspension. Visual observation of the suspension detected scattered light and the formation of particulate matter in the liquid. The suspension was subjected to centrifugal separation at 1500 rpm for 30 minutes, and the supernatant was recovered. The supernatant was further subjected to centrifugal separation at 1500 rpm for 30 minutes, and deposited coarse particles were removed. Subsequently, the recovered supernatant was subjected to centrifugal separation at 6000 rpm for 30 minutes, and the supernatant was removed. Water was added to the deposit, followed by centrifugal separation at 6000 rpm for 30 minutes to clean the deposit in the form of fine particles, thereby obtaining luminescent particles (example particles 1). The above process was performed in the atmospheric environment, and ultrapure water (Milli-Q water), produced by using an ultrapure water apparatus (manufactured by Millipore Co.), was used for the preparation of the aqueous dispersion of the emulsion material and for the cleaning of the fine particles. FIG. 1 shows a scanning electron micrograph (SEM image: 7500 times) of the example particles 1 obtained. The diameters of the example particles 1 were measured by a dynamic light scattering method. As a result, the example particles 1 were found to have an average particle diameter of 517 nm, and a polydispersion index of 0.213.

A luminescent particle production process was performed in the same manner as described above except for using mCBP (melting point: 267° C.) instead of mCP, thereby obtaining luminescent particles. The particles had very poor water dispersibility. The particles were found to have a microcrystalline structure. The results revealed that the formation of particles via the formation of an emulsion is important in obtaining spherical particles having high water dispersibility.

(Example 2) Production of Luminescent Particles Using 4CzIPN in a Different Amount Luminescent particles (example particles 2) were produced in the same manner as in Example 1 except for changing the content of 4CzIPN in the liquid mixture to 2% by weight based on the total amount of mCP and 4CzIPN. The luminescent particles produced contained particles having a maximum diameter of less than 100 nm.

(Example 3) Production of Luminescent Particles Performed with Varying mCP/DSPE-PEG2K Ratios Luminescent particles were produced in the same manner as in Example 1 except for changing the molar content ratio of mCP to DSPE-PEG2K (mCP/DSPE-PEG2K) in the emulsion to 1.0, 10, 20, or 100. The luminescent particles produced with the content ratio 1.0 contained particles having a maximum diameter of less than 100 nm. There was found no significant difference in the maximum diameter of the resulting particles between the varying content rations.

(Example 4) Production of Luminescent Particles Under Low-Oxygen Conditions

Luminescent particles (example particles 4) were produced in the same manner as in Example 1 except that the aqueous dispersion of the emulsion material was prepared using degassed water produced by freezing/degassing, and that the entire process until the obtainment of particulate matter through cooling of the emulsion was performed in a nitrogen atmosphere. The molar content ratio of mCP to DSPE-PEG2K (mCP/DSPE-PEG2K) in the emulsion was 10. The production of the degassed water by freezing/degassing was performed by first repeating the following steps (1) to (3) five times: (1) freezing water in a container with liquid nitrogen, (2) bringing the interior of the container into a depressurized state, and (3) returning the temperature in the container to room temperature to melt the water, and then replacing the internal atmosphere of the container with argon.

The luminescent particles produced in Example 4 contained particles having a maximum diameter of less than 1000 nm. The PL quantum yield of the luminescent particles was as high as 94%.

(Example 5) Control of Particle Size by Application of Ultrasonic Waves

Luminescent particles were produced in the same manner as in Example 4 except that after the preparation of the aqueous dispersion of the emulsion material and before the heating of the aqueous dispersion at a high pressure, ultrasonic waves (20 kHz, intensity 100 W) were applied to the aqueous dispersion for 60 minutes.

Figure 4:
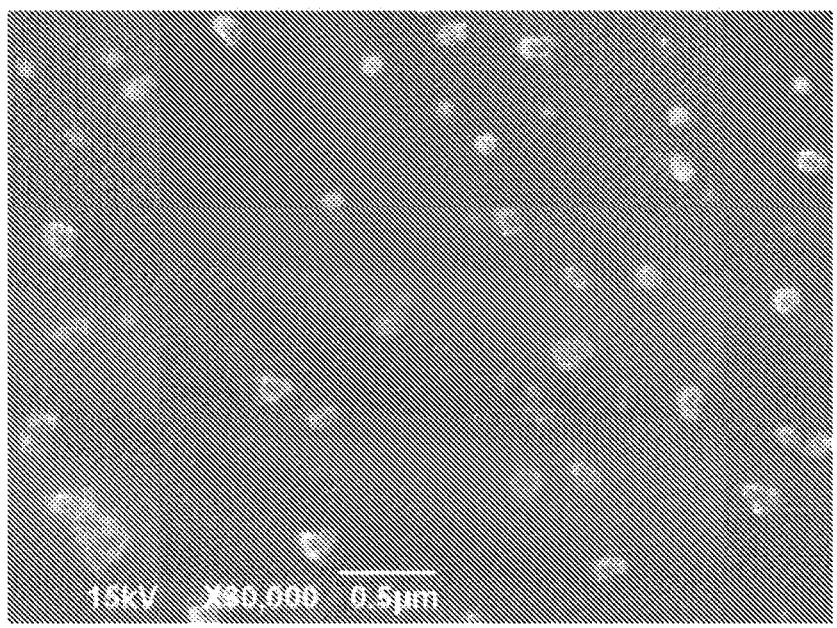
FIG. 4 is a scanning electron micrograph of luminescent particles produced in Example 5.

The luminescent particles produced in Example 5 contained a considerable proportion of particles having a maximum diameter of less than 200 nm, and also contained particles having a maximum diameter of less than 100 nm (see FIG. 4). The proportion of particles having a small maximum diameter in the luminescent particles was higher than the luminescent particles produced in Examples 1 and 4. This verifies that the particle size (diameter) can be controlled by the application of ultrasonic waves.

(Example 6) Control of Particle Size by Adjustment of the Concentration of Surfactant Luminescent particles were produced in the same manner as in Example 5 except that when mCP as a host material, 4CzIPN as an organic luminescent material, and DSPE-PEG2K as a surfactant were placed in a vial to prepare a liquid mixture, a mixed solvent of methanol and chloroform (volumetric ratio 1:9) was used as a solvent, and that the host material and the surfactant were used at varying molar ratios.

As a result, it was found that by using the mixed solvent upon the production of the film of the mixture before the preparation of the aqueous dispersion, Rayleigh scattering after the preparation of the aqueous dispersion was prevented, and that the diameters of the luminescent particles were effectively reduced and the water dispersibility of the luminescent particles was enhanced. Further, by making the concentration of the host material $1/10$ of that in Example 5, and making the molar ratio between the host material and the surfactant 1:5, luminescent particles having a maximum diameter of less than 100 nm were produced in a higher proportion. This indicates that the diameters of the luminescent particles can be controlled by controlling the molar ratio between the host material and the surfactant. This also indicates that the diameters of the luminescent particles can be controlled with the overall concentration of the system as dissolved in the mixed solvent.

Further, the concentration of the surfactant in the liquid mixture and the time for applying ultrasonic waves after the preparation of the aqueous dispersion of the emulsion material were varied to examine how the variation changes the diameters of the resulting luminescent particles. As a result, it was found that the use of the surfactant at an increased concentration can produce luminescent particles having a small diameter even when the time for applying ultrasonic waves is reduced.

(Comparative Example 1) Production of Luminescent Particles Using 4CzIPN (Organic Luminescent Material) and DSPE-PEG2K (Surfactant)

A tetrahydrofuran solution (1 mL) of 4CzIPN (1.3 μmol) as an organic luminescent material and DSPE-PEG2K (0.71 μmol) as a surfactant was placed in a vial, and stirred for 4 hours in a nitrogen atmosphere. A 4:1 mixed solvent (2 mL) of tetrahydrofuran and water was added to the solution, and ultrasonic treatment of the solution was performed for 3 minutes. Thereafter, water (7 mL) was added to the solution while performing the ultrasonic treatment, and the ultrasonic treatment was further performed. After vaporizing and removing tetrahydrofuran from the solution, the solution was filtered with a filter having a pore size of 0.22 and the reside was freeze-dried to obtain dried particles. Water was added to the dried particles, followed by 2-minute ultrasonic treatment to obtain an aqueous dispersion of fine particles (comparative particles 1).

Comparative Example 2

Water-soluble quantum dots QD450 (emission wavelength 450 nm, CdSe/ZnS core-shell type quantum dots PEG functionalized, manufactured by Aldrich) were provided as comparative particles 2.

[Evaluation of Luminescence Properties]

The example particles 1, the example particles 2 and the comparative particles 1 were separately dispersed in water to prepare three aqueous dispersions (0.05 µg/L). For each of the aqueous dispersions and a toluene solution of 4CzIPN ($1.0 \times 10^{-5}$ mol/L), the emission maximum wavelength, the PL quantum yield (photoluminescence quantum yield) and the emission lifetime $\tau_1$, $\tau_2$ were measured using 340-nm excitation light. The results are shown in table 1 below.

were produced using degassed water, had a PL quantum yield of 94%, indicating that the luminescence property of the luminescent particles is very high. This indicates a significant influence of oxygen trapped in particles.

[Cell Test]

The example particles 1 were introduced into HEK293 cells (cancer cells derived from human fibroblast cells), and the uptake and the cytotoxicity were evaluated.

First, HEK293 cells were sown in a culture medium, and cultured at 37° C. in the presence of 5% $CO_2$ until the cells became subconfluent (a state in which the cell density is about ⅘ of the saturation density). The example particles 1 were added to the culture medium, and the cells were incubated for 24 hours at 37° C. in the presence of 5% $CO_2$. The cells after incubation were divided into two groups. One group of cells were diluted 16 times and observed with a microscope, while the other group of cells were subcultured, and cultured at 37° C. in the presence of 5% $CO_2$ until the cells became subconfluent to obtain first-passage cells. The cultured cells were divided into two groups. One group of cells were observed with a microscope, while the other group of cells were subcultured, and cultured until the cells became subconfluent (at 37° C. in the presence of 5% $CO_2$). This operation was repeated three times to sequentially cultivate second-passage to fourth-passage cells. The period from the first passage to the fourth passage was 7 days.

TABLE 1

| Measurement sample | Measurement conditions | Emission maximum wavelength (nm) | PL quantum Yield (%) | Emission lifetime $\tau_1$ (ns) | Emission lifetime $\tau_2$ (µs) |
|---|---|---|---|---|---|
| Toluene solution of 4CzIPN | Before nitrogen bubbling | 505 | 21 | 11 | 0.31 |
| | After nitrogen bubbling | 505 | 83 | 16 | 4.71 |
| Aqueous dispersion of comparative particles 1 | Before nitrogen bubbling | 550 | 15 | 13 | 1.48 |
| | After nitrogen bubbling | 550 | 12 | 15 | 1.94 |
| Aqueous dispersion of example particles 1 | Before nitrogen bubbling | 515 | 64 | 18 | 3.09 |
| | After nitrogen bubbling | 515 | 64 | 18 | 3.10 |
| Aqueous dispersion of example particles 2 | Before nitrogen bubbling | 510 | 57 | 15 | 3.13 |
| | After nitrogen bubbling | 510 | 57 | 15 | 3.13 |
| Aqueous dispersion of example particles 4 | Before nitrogen bubbling | 515 | 94 | 17 | 3.13 |
| | After nitrogen bubbling | 515 | 94 | 17 | 3.13 |

Figure 2:
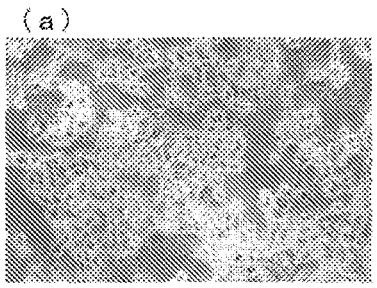
FIGS. 2(a) through 2(f) are micrographs showing the example particles 1 which have been taken into HEK293 cells.
Figure 2:
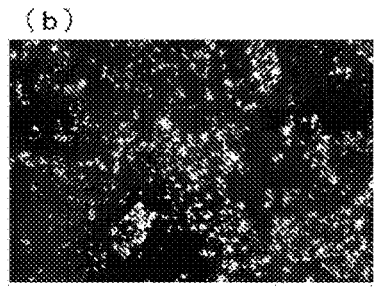
Figure 2:
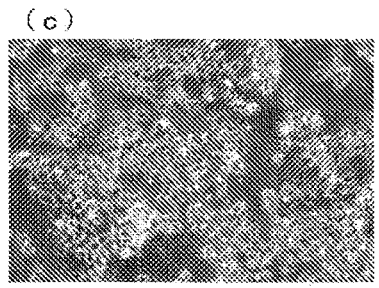
Figure 2:
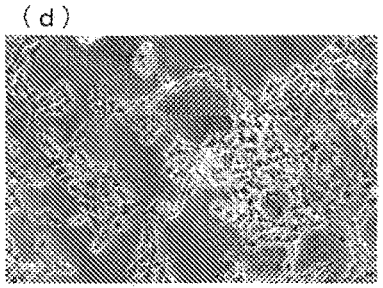
Figure 2:
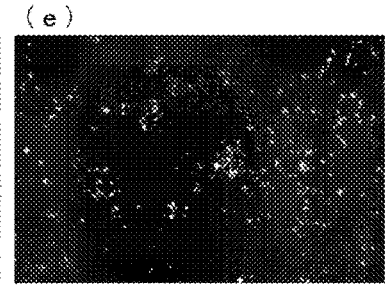
Figure 2:
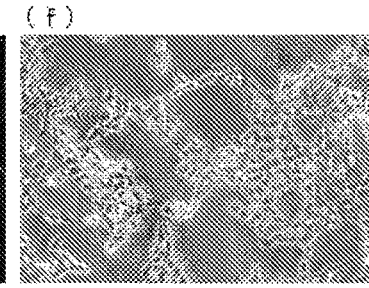

As shown in Table 1, compared to the toluene solution of 4CzIPN, the aqueous dispersion of comparative particles 1, not containing mCP, had a significantly longer emission wavelength and a significantly lower PL quantum yield. This is considered to be due to the fact that because of amorphous association of 4CzIPN and contact with water, the comparative luminescent particles were affected by the polarity of water. On the other hand, the aqueous dispersions of example particles 1 and 2 each had an emission wavelength comparable to that of the toluene solution of 4CzIPN, and had a high PL quantum yield. The data thus verifies that the combined use of the host material and the organic luminescent material to constitute luminescent particles can prevent the influence of molecular association and of the polarity of water, thereby significantly enhancing the luminescence properties of the luminescent particles. The data also shows that the aqueous dispersion of example particles 4, which FIGS. 2(a) to 2(c) show micrographs of the HEK293 cells after the addition of the example particles 1 and 24-hour incubation, and FIGS. 2(d) to 2(f) show micrographs of the HEK293 cells after the addition of the example particles 1 and 7-day (4-passage) culture. FIGS. 2(a) and 2(d) are bright-field images of the HEK293 cells before irradiation with excitation light, FIGS. 2(b) and 2(e) are fluorescent images of the HEK293 cells, which were taken while irradiating the cells with 400-nm excitation light, FIG. 2(c) is a bright-field fluorescent image which was taken while irradiating the cells with excitation light in the field of FIG. 2(a), and FIG. 2(f) is a bright-field fluorescent image which was taken while irradiating the cells with excitation light in the field of FIG. 2(d).

The luminescence shown in FIGS. 2(b), 2(c), 2(e) and 2(f) derives from the example particles 1. In FIGS. 2(c) and 2(f), the area in which the cells exist overlaps the luminescent area. This indicates that the example particles 1 were well taken into the HEK293 cells. It was found that also in micrographic images of the first-passage to third-passage cells, the area in which the cells exist overlaps the luminescent area. The test results thus verify that the example particles 1, which had been taken into the HEK293 cells, existed stably in the cells over 4 passages/7 days, did not exhibit any cytotoxicity, and had excellent traceability.

In a comparative test, the comparative particles 1 were introduced into HEK293 cells. As a result, most of the HEK293 cells peeled off the wall of a petri dish in two hours. This indicates high cytotoxicity of the comparative particles 1.

In a cell test conducted on HeLa cells (cells derived from human cervical cancer), both of the example particles 1 and the comparative particles 1 were taken into the cells. It was found that the degree of the uptake of the example particles 1 tends to be higher than that of the comparative particles 1 and, in addition, the luminescence of the example particles 1 tends to be stronger than that of the comparative particles 1.

[Evaluation of Light Stability]

Figure 3:
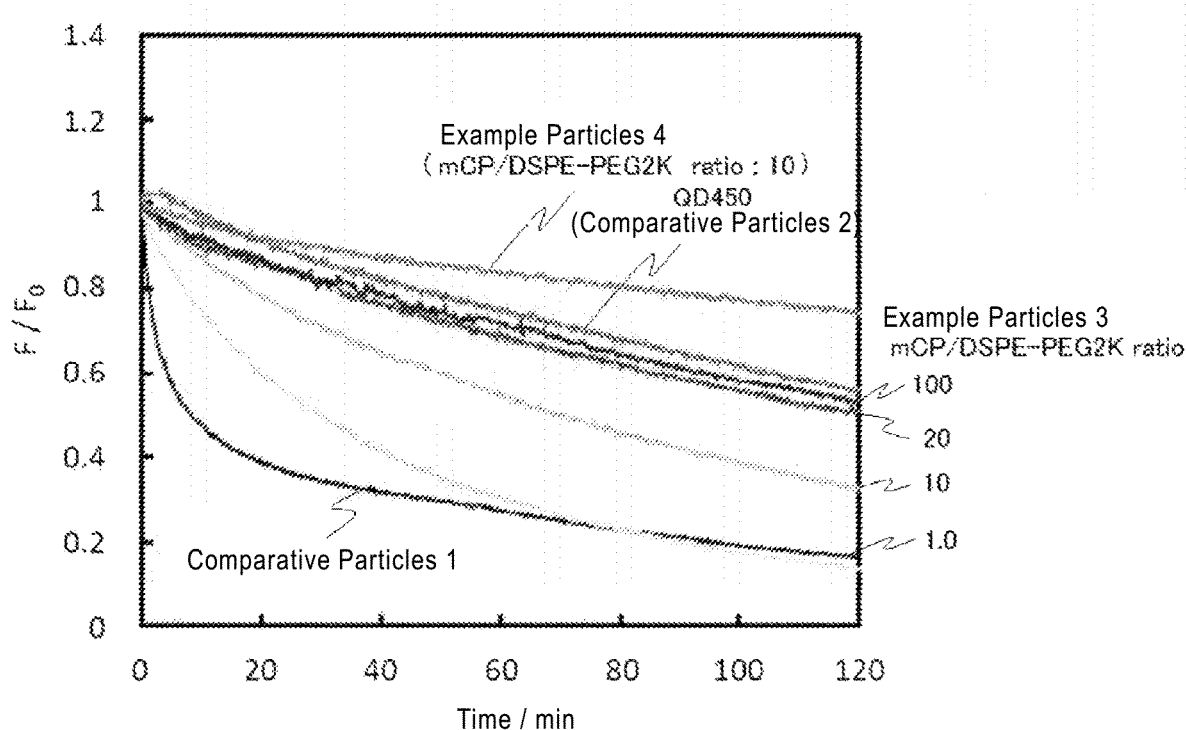
FIG. 3 is a graph showing the results of an evaluation of light stability, performed on luminescent particles produced in Examples 3 and 4 and on comparative particles 1 and 2.

The luminescent particles produced in Examples 3 and 4, the comparative particles 1 and the QD450 particles (comparative particle 2) were irradiated with light, having a spectral distribution in the wavelength range of 300 to 400 nm, at 5 mW/cm² for 2 hours, and the time-dependent change of the emission intensity during the light irradiation was determined. The results are shown in FIG. 3. The wavelength of detected light was 515 nm for the luminescent particles produced in Examples 3 and 4 and Comparative Example 1, and 450 nm for the QD450 particles. In FIG. 3, $F/F_0$ represents the ratio of an emission intensity F at an elapsed time to an initial emission intensity $F_0$. The numerical values on the right side of FIG. 3 show the molar content ratios of mCP to DSPE-PEG2K (mCP/DSPE-PEG2K) in the various types of luminescent particles produced in Example 3.

As can be seen in FIG. 3, the mCP-containing luminescent particles produced in Examples 3 and 4 had higher light stability than the comparative particles 1 containing no mCP. As can also be seen in FIG. 3, the light stability of the luminescent particles increases with increase in the mCP/DSPE-PEG2K ratio. The data thus indicates that the host material/surfactant ratio is preferably not less than 1, more preferably not less than 10, and even more preferably not less than 20. The data also shows that the light stability of the luminescent particles (example particles 4) of Example 4, produced in a nitrogen atmosphere using degassed water, was higher than those of the various types of luminescent particles of Example 3 which were produced in the atmospheric environment using ultrapure water, and even higher than the light stability of QD450. This verifies that the production of luminescent particles is preferably performed using degassed water and a low-oxygen atmosphere.

(Example 6) Production of Luminescent Particles Using mCP (Host Material), 4CzBN (Assist Dopant), DABNA2 (Organic Luminescent Material), and DSPE-PEG2K (Surfactant)

Using mCP (melting point: 178° C.) as a host material, 4CzBN as an assist dopant, DABNA2 as an organic luminescent material, and DSPE-PEG2K (distearoylphophatidyl ethanolamine-polyethylene glycol 2000) as a surfactant, luminescent particles were produced by the same method as used in Example 1. 4CzBN was used in an amount which was 15% by weight of the amount of mCP, and DABNA2 was used in an amount which was 1% by weight of the amount of mCP.

Figure 5:
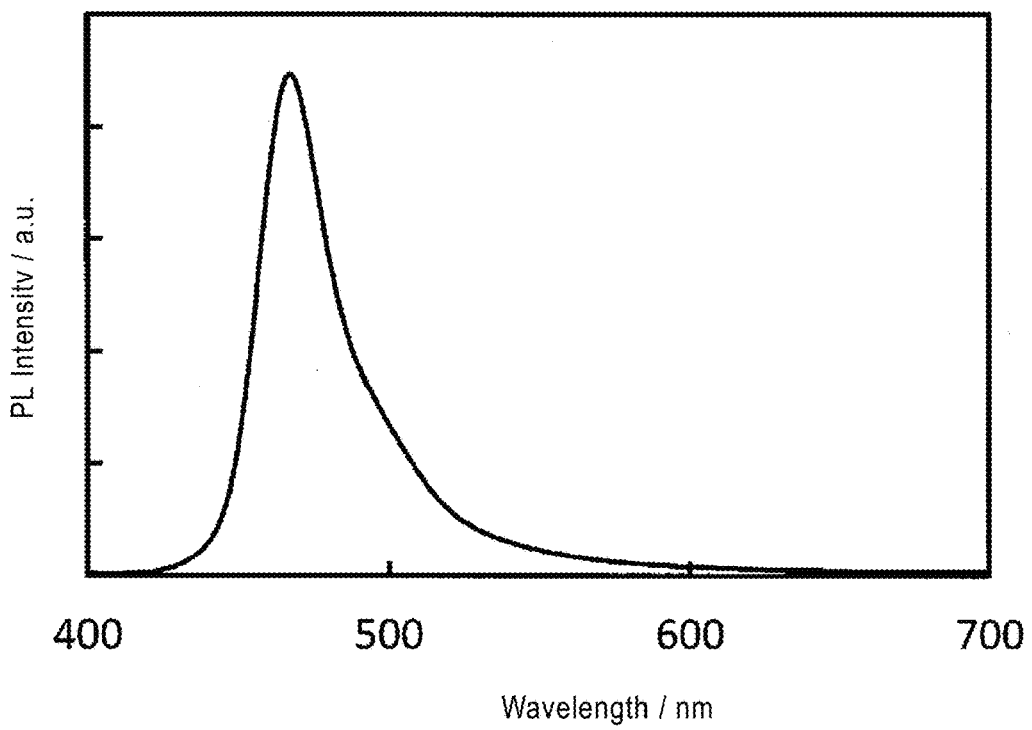
FIG. 5 shows the emission spectrum of luminescent particles produced in Example 6.
Figure 6:
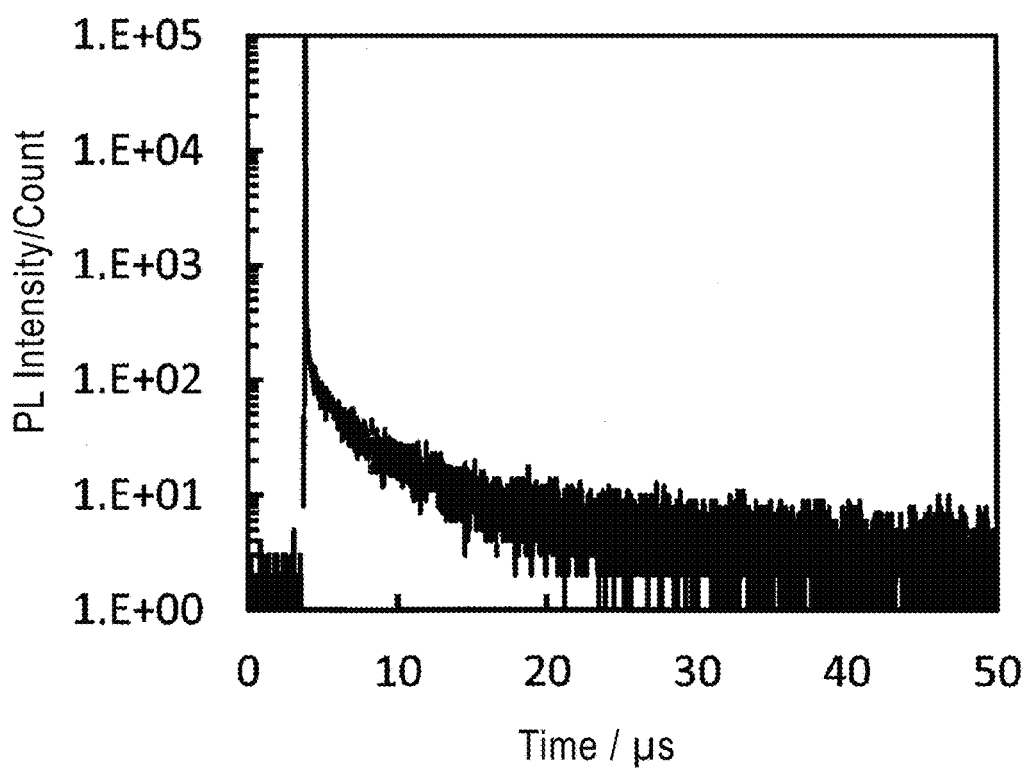
FIG. 6 shows the transient decay curve of the luminescent particles produced in Example 6.

The resulting luminescent particles contained particles having a maximum diameter of less than 1000 nm. The resulting luminescent particles were dispersed in water to prepare an aqueous dispersion (0.05 µg/L). The aqueous dispersion was subjected to measurement of the emission spectrum with 340-nm excitation light. The results are shown in FIG. 5, and the transient decay curve is shown in FIG. 6. As can be seen in FIG. 5, luminescence from DABNA2 was observed at a maximum wavelength of 467 nm, whereas luminescence from 4CzBN was not observed. The full width at half maximum (FWHM) was as narrow as 29 nm. As can be seen in FIG. 6, radiation of delayed fluorescence was also observed. The PL quantum yield (photoluminescence quantum yield) was found to be 45%. The results indicate efficient transfer of energy from 4CzBN as an assist dopant to DABNA2 as an organic luminescent material.

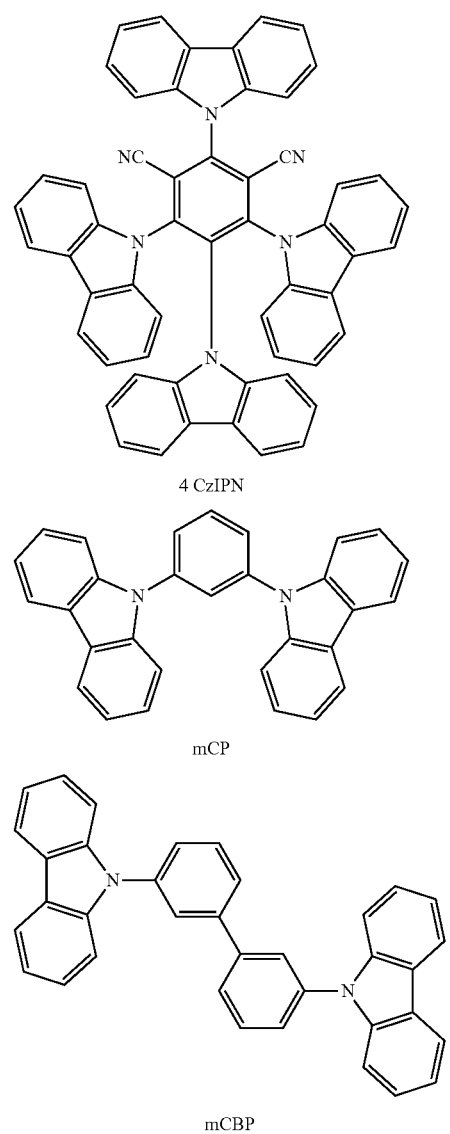

4 CzIPN mCP mCBP

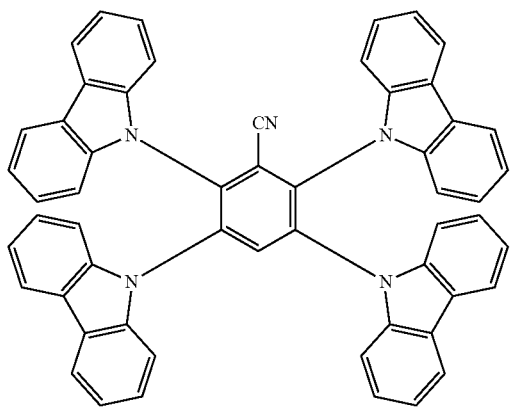

4 CzBN

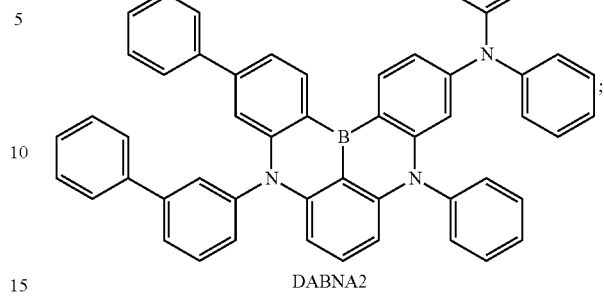

DABNA2 an assist dopant having the following structure:

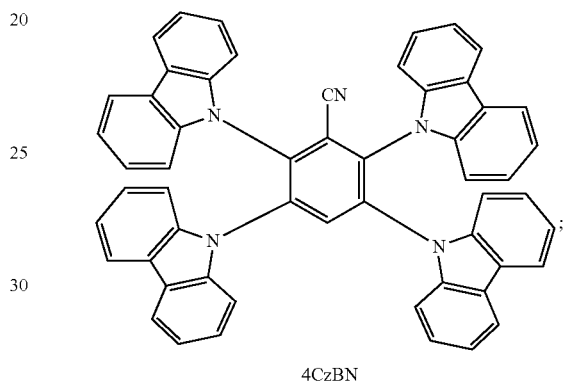

4CzBN and
distearoylphophatidyl ethanolamine-polyethylene glycol as a surfactant, wherein the host material is a compound having a structure in which a benzene ring or a biphenyl ring is substituted with a carbazolyl group, and wherein the luminescent particles are produced by stirring an emulsion material, including the host material, the organic luminescent material, the assist dopant, the surfactant and water, under conditions that melt the host material, thereby forming an emulsion; and then cooling the emulsion.

2. The luminescent particles according to claim 1, wherein the organic luminescent material is a delayed fluorescence material.

3. The luminescent particles according to claim 1, wherein the host material is a compound having a structure in which a biphenyl ring is substituted with a carbazolyl group.

4. The luminescent particles according to claim 1, wherein the assist dopant is a delayed fluorescence material.

5. The luminescent particles according to claim 1, wherein the molar content ratio of the host material to the surfactant (host material/surfactant) is not less than 20.

6. A bioimaging composition comprising the luminescent particles according to claim 1.

7. Luminescent particles according to claim 1, wherein the host material has a melting point of 40 to 200° C. at atmospheric pressure.

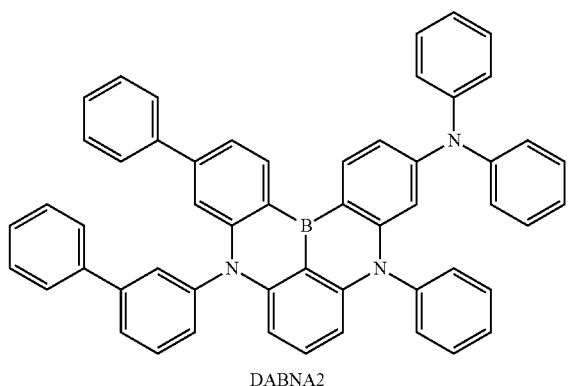

DABNA2

INDUSTRIAL APPLICABILITY

The luminescent particle production method of the present invention can produce luminescent particles which, despite no inclusion of any heavy metal element, exhibit high luminous efficiency even in water and have high light stability. Further, the use of a delayed fluorescence material as a luminescent material can impart long-life luminescence to the luminescent particles. The use of the thus-produced luminescent particles can provide a bioimaging material which is highly safe and which enables clear imaging of the distribution or the dynamics of living cells or a biological substance. Therefore, the present invention is highly applicable industrially.

The invention claimed is:

1. Luminescent particles with a maximum diameter of less than 100 μm, comprising:
   a glassy host material having a melting point;
   an organic luminescent material containing no heavy metal element and having the following structure:

* * * * *